US007445645B2

(12) United States Patent
Sabelle et al.

(10) Patent No.: US 7,445,645 B2
(45) Date of Patent: *Nov. 4, 2008

(54) ORTHO-AND/OR META-SUBSTITUTED N-ALKYLHYDROXYLATED SECONDARY PARA-PHENYLENEDIAMINE COMPOUNDS, COMPOSITIONS FOR DYEING KERATIN FIBERS COMPRISING SUCH COMPOUNDS, AND PROCESSES OF DYEING THEREWITH

(75) Inventors: Stéphane Sabelle, Paris (FR); Philippe Breton, Noisy le Roy (FR); Alex Junino, Livry Gargan (FR)

(73) Assignee: L'Oreal S.A., Paris (FR)

( * ) Notice: Subject to any disclaimer, the term of this patent is extended or adjusted under 35 U.S.C. 154(b) by 37 days.

This patent is subject to a terminal disclaimer.

(21) Appl. No.: 11/067,173

(22) Filed: Feb. 28, 2005

(65) Prior Publication Data
US 2006/0026774 A1    Feb. 9, 2006

Related U.S. Application Data

(60) Provisional application No. 60/569,631, filed on May 11, 2004.

(30) Foreign Application Priority Data
Feb. 27, 2004    (FR)    .................................. 04 02019

(51) Int. Cl.
*A61Q 5/10*    (2006.01)
*C07C 211/00*    (2006.01)

(52) U.S. Cl. ....................... 8/405; 8/406; 8/407; 8/408; 8/410; 8/411; 8/415; 8/416; 8/421; 564/388; 564/389

(58) Field of Classification Search ................ 8/405, 8/406, 407, 408, 410, 411, 415, 416, 421; 564/388, 389
See application file for complete search history.

(56) References Cited

U.S. PATENT DOCUMENTS

| 4,003,699 | A |  | 1/1977 | Rose et al. |  |
| RE30,199 | E |  | 1/1980 | Rose et al. |  |
| 4,330,291 | A | * | 5/1982 | Bugaut et al. .................. | 8/406 |
| 4,823,985 | A |  | 4/1989 | Grollier et al. |  |
| 5,026,401 | A |  | 6/1991 | Bugaut et al. |  |
| 5,061,289 | A |  | 10/1991 | Clausen et al. |  |
| 5,096,455 | A |  | 3/1992 | Grollier |  |
| 5,167,669 | A | * | 12/1992 | Grollier .......................... | 8/405 |
| 5,380,340 | A |  | 1/1995 | Neunhoeffer et al. |  |
| 5,534,267 | A |  | 7/1996 | Neunhoeffer et al. |  |
| 5,663,366 | A |  | 9/1997 | Neunhoeffer et al. |  |
| 5,708,151 | A |  | 1/1998 | Möckli |  |
| 5,760,576 | A |  | 6/1998 | Ouchi |  |
| 6,099,592 | A |  | 8/2000 | Vidal et al. |  |
| 6,284,003 | B1 |  | 9/2001 | Rose et al. |  |
| 6,338,741 | B1 |  | 1/2002 | Vidal et al. |  |
| 6,645,288 | B1 |  | 11/2003 | Dargaud et al. |  |
| 6,730,789 | B1 |  | 5/2004 | Birault et al. |  |

FOREIGN PATENT DOCUMENTS

| DE | 23 59 399 | 6/1975 |
| DE | 38 43 892 | 6/1990 |
| DE | 41 33 957 | 4/1993 |
| DE | 195 43 988 | 5/1997 |
| EP | 0 714 954 | 6/1996 |
| EP | 0 770 375 | 5/1997 |
| EP | 1 093 790 | 4/2001 |
| FR | 2 519 643 | 7/1983 |
| FR | 2 586 913 | 3/1987 |
| FR | 2 649 886 | 1/1991 |
| FR | 2 733 749 | 11/1996 |
| FR | 2 801 308 | 5/2001 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |

OTHER PUBLICATIONS

STIC Search Report dated Mar. 27, 2007.*
English Language DERWENT Abstract for EP 0 770 375, May 2, 1997.
English Language DERWENT Abstract for EP 1 093 790, Apr. 25, 2001.
English Language DERWENT Abstract for JP 2-19576, Jan. 23, 1990.
English Language DERWENT Abstract for JP 5-163124, Jun. 29, 1993.
French Search Report for FR 04/02019 mailed Sep. 27, 2004 (the French Priority Application for U.S. Appl. No. 11/067,173,the present application) Ex. Bedel.
Carswell et al., "Growth kinetics of polydiacetylene films prepared in micrgravity," *ACS Symposium Series* 793: 51-64 (2001), Chemical Abstract No. XP002297620.
Kotsuki et al., "High pressure organic chemistry; XII. A convenient synthesis of aromatic amines for activated aromatic fluorides," *Synthesis*, 12: 1147-1148 (1990).
Massa & Artico, "Spiro-[4H-pyrrolo[1,2-a][1,4]benzodiazepine-4,4'-piperidine] derivatives as potential nootropic agents: a simple one pot synthesis," *Synth. Commun.*, 20(22): 3537-3543 (1990).

* cited by examiner

Primary Examiner—Eisa B Elhilo
(74) Attorney, Agent, or Firm—Finnegan, Henderson, Farabow, Garrett & Dunner L.L.P.

(57) ABSTRACT

The present disclosure relates to novel N-alkylhydroxylated secondary para-phenylenediamine compounds, to a composition for dyeing keratin fibers, for instance human keratin fibers such as the hair, comprising, in a medium that is suitable for dyeing, at least one ortho- and/or meta-substituted N-alkylhydroxylated secondary para-phenylenediamine, to a process for dyeing keratin fibers comprising applying this composition, and also a dyeing "kit."

26 Claims, No Drawings

ORTHO- AND/OR META-SUBSTITUTED N-ALKYLHYDROXYLATED SECONDARY PARA-PHENYLENEDIAMINE COMPOUNDS, COMPOSITIONS FOR DYEING KERATIN FIBERS COMPRISING SUCH COMPOUNDS, AND PROCESSES OF DYEING THEREWITH

CROSS-REFERENCE TO RELATED APPLICATIONS

This application claims benefit of U.S. Provisional Application No. 60/569,631, filed May 11, 2004, and French Patent Application No. 04/02019, filed Feb. 27, 2004, the contents of both of which are incorporated herein by reference.

FIELD OF THE INVENTION

The present disclosure relates to a novel family of ortho-substituted and/or meta-substituted N-alkylhydroxylated secondary para-phenylenediamine compounds and to their use for dyeing keratin fibers, for instance human keratin fibers such as the hair.

BACKGROUND OF THE INVENTION

It is known practice to dye keratin fibers, such as human hair, with dye compositions comprising oxidation dye precursors, such as ortho- or para-phenylenediamines, ortho- or para-aminophenols, and heterocyclic compounds, which are generally referred to as oxidation bases. These oxidation bases can be colorless or weakly colored compounds which, when combined with oxidizing products, may give rise to colored compounds by a process of oxidative condensation. It is also known that the shades obtained with these oxidation bases may be varied by combining them with couplers or coloration modifiers, wherein the coloration modifiers can be chosen from, for example, meta-diaminobenzenes, meta-aminophenols, meta-diphenols and certain heterocyclic compounds such as indole compounds. The variety of molecules used as oxidation bases and couplers makes it possible to obtain a wide range of colors.

The "permanent" coloration that can be obtained by these oxidation dyes, moreover, may satisfy at least one of a number of requirements. For example, it may not have toxicological drawbacks, it may be able to allow shades of the desired intensity to be obtained, and may be able to have good resistance to external agents such as light, bad weather, washing, permanent waving, perspiration and rubbing. The dyes may also be able to allow white hairs to be covered and, lastly, they may be as unselective as possible, that is to say that they may be able to allow the smallest possible differences in coloration to be produced over the entire length of the same keratin fiber, which is generally differently sensitized (that is to say damaged) between its end and its root.

SUMMARY OF THE INVENTION

The inventor has discovered, surprisingly and advantageously, that it is possible to obtain novel compositions for dyeing keratin fibers, for instance human keratin fibers such as the hair, which, in one embodiment, are capable of giving strong, aesthetic and sparingly selective colorations in varied shades, and which, in a further embodiment, are capable of showing good resistance to the various attacking factors to which the fibers may be subjected, by using at least one ortho-substituted and/or meta-substituted N-alkylhydroxylated secondary para-phenylenediamine. In one embodiment, these compositions have a good toxicological profile.

Accordingly, the present disclosure relates to a family of ortho-substituted and/or meta-substituted N-alkylhydroxylated secondary para-phenylenediamine compounds, to processes for synthesizing them and to their uses, for example, for dyeing keratin fibers, for instance, human keratin fibers such as the hair. The present disclosure further relates to a composition comprising at least one ortho-substituted and/or meta-substituted N-alkylhydroxylated secondary para-phenylenediamine, dyeing processes using this composition, the uses of the composition according to the present disclosure for dyeing keratin fibers, for instance human keratin fibers such as the hair, and for example, multi-compartment devices or dye "kits."

The composition of the present disclosure makes it possible, for instance, to obtain very powerful, sparingly selective and color-fast, such as light-fast, dyeing of keratin fibers, while at the same time avoiding the degradation of the fibers.

Other characteristics, aspects, objects and benefits of the present disclosure will emerge even more clearly upon reading the description and the examples that follow.

As used herein, the term "alkyl" is understood to mean a linear or branched $C_1$-$C_{10}$ radical, for example the following linear or branched radicals: methyl, ethyl, propyl, butyl, pentyl, hexyl, octyl, etc.

DETAILED DESCRIPTION OF THE INVENTION

The novel ortho-substituted and/or meta-substituted N-alkylhydroxylated secondary para-phenylenediamine compounds according to the present disclosure are compounds of formula (I):

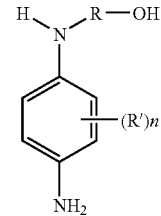

wherein:

R is chosen from linear and branched $C_3$-$C_{10}$ alkylene radicals, optionally substituted with at least one group chosen from amino, monoalkylamino, dialkylamino, alkylcarbonyl, amido, monoalkylaminocarbonyl and dialkylaminocarbonyl groups, and wherein the alkylene radicals are optionally interrupted with at least one heteroatom chosen from nitrogen and oxygen, R' is chosen from alkyl, alkoxy, hydroxyalkoxy, alkoxyalkyl, monohydroxyalkyl and polyhydroxyalkyl radicals and a chlorine atom, n is an integer from 1 to 4.

According to one embodiment of the present disclosure, R may be chosen from linear and branched $C_3$-$C_8$, such as $C_3$-$C_6$ alkylene radicals.

According to another embodiment, R may be chosen from linear and branched $C_3$-$C_6$, such as $C_3$-$C_4$ alkylene radicals interrupted with a nitrogen or oxygen atom.

For example, R' may be chosen from $C_1$-$C_3$ alkyl and $C_1$-$C_3$ alkoxy groups, and, for instance, may be a methyl group.

For further example, n may be equal to 1 or 2, and in one embodiment of the present disclosure, n is equal to 1.

The compounds of formula (I) may be in free form or in the form of salts, such as the addition salts with an acid, which can be chosen from, for example, the hydrochlorides, hydrobromides, sulfates, citrates, succinates, tartrates, lactates, tosylates, benzenesulfonates, phosphates and acetates.

For further instance, among the compounds of formula (I), non-limiting mention may be made of those listed in the table below:

| | |
|---|---|
| 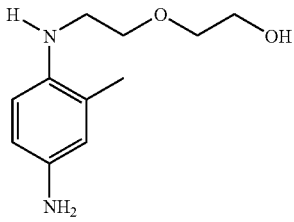 | 2-[2-(4-amino-2-methylphenylamino)-ethoxy]ethanol |
| 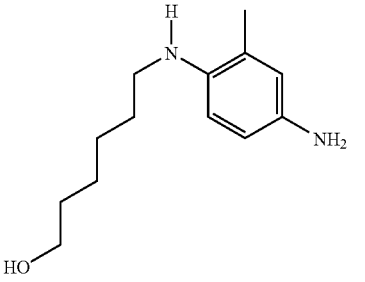 | 2-[2-(4-amino-2-methylphenylamino)ethylamino]ethanol |
| 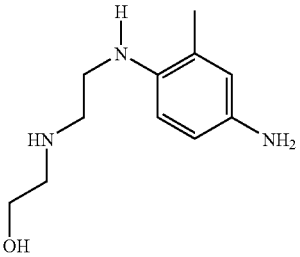 | 3-(4-amino-2-methylphenylamino)propan-1-ol |
| 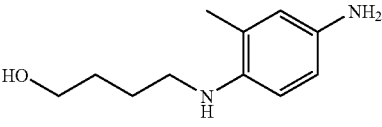 | 2-(4-amino-2-methylphenylamino)hexan-1-ol |
| 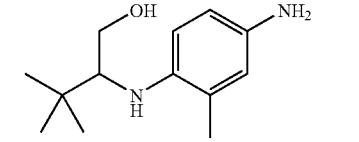 | 1-(4-amino-2-methylphenylamino)butan-2-ol |
| 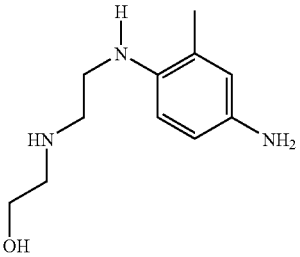 | 3-(4-amino-2-methylphenylamino)-2,2-dimethylpropan-1-ol |

-continued

| | |
|---|---|
| 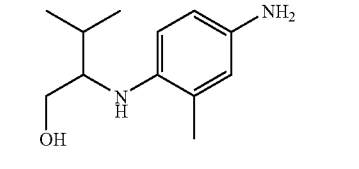 | 6-(4-amino-2-methylphenylamino)hexan-1-ol |
| 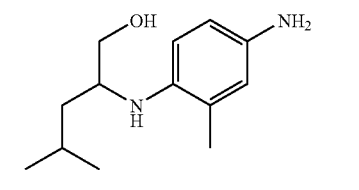 | 4-(4-amino-2-methylphenylamino)butan-1-ol |
| 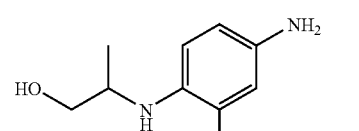 | 2-(4-amino-2-methylphenylamino)-3,3-dimethylbutan-1-ol |
| 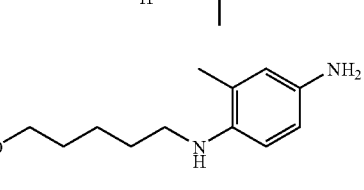 | 2-(4-amino-2-methylphenylamino)-3-methylbutan-1-ol |
|  | 2-(4-amino-2-methylphenylamino)-4-methylpentan-1-ol |
| 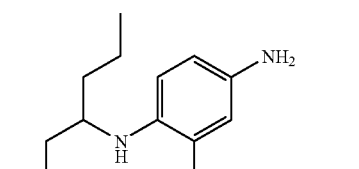 | 2-(4-amino-2-methylphenylamino)-propan-1-ol |
| 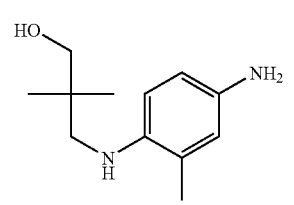 | 5-(4-amino-2-methylphenylamino)pentan-1-ol |
| 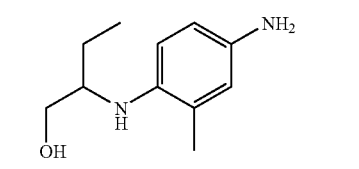 | 2-(4-amino-2-methylphenylamino)pentan-1-ol |
| | 2-(4-amino-2-methylphenylamino)butan-1-ol |

-continued

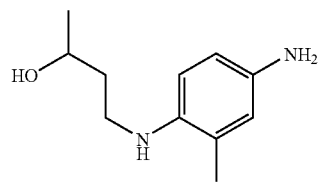 4-(4-amino-2-methylphenylamino)butan-2-ol

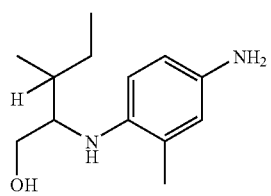 2-(4-amino-2-methylphenylamino)-3-methylpentan-1-ol

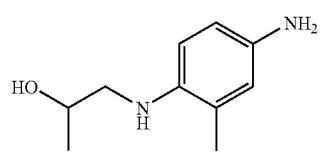 1-(4-amino-2-methylphenylamino)propan-2-ol

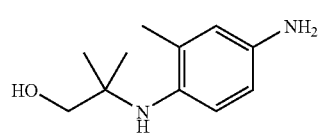 2-(4-amino-2-methylphenylamino)-2-methylpropan-1-ol

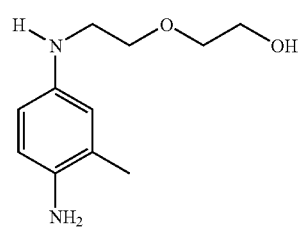 2-[2-(4-amino-3-methylphenylamino)ethoxy]ethanol

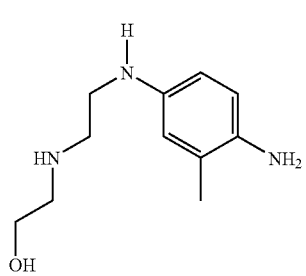 2-[2-(4-amino-3-methylphenylamino)-ethylamino]ethanol

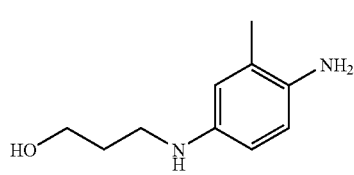 3-(4-amino-3-methylphenylamino)propan-1-ol

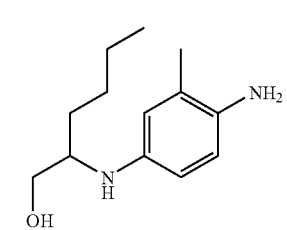 2-(4-amino-3-methylphenylamino)hexan-1-ol

-continued

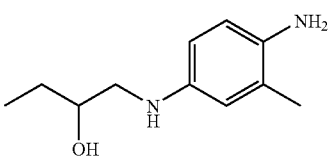 1-(4-amino-3-methylphenylamino)butan-2-ol

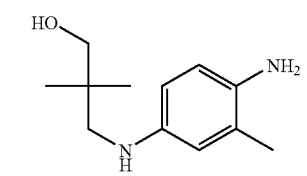 3-(4-amino-3-methylphenylamino)-2,2-dimethylpropan-1-ol

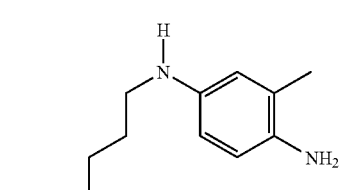 6-(4-amino-3-methylphenylamino)hexan-1-ol

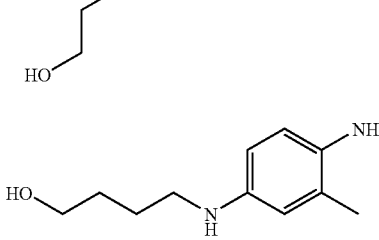 4-(4-amino-3-methylphenylamino)butan-1-ol

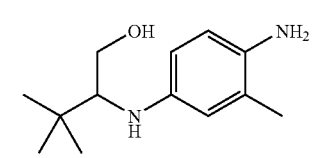 2-(4-amino-3-methylphenylamino)-3,3-dimethylbutan-1-ol

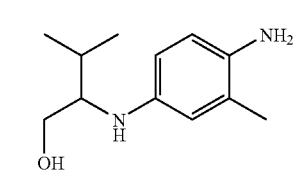 2-(4-amino-3-methylphenylamino)3-methylbutan-1-ol

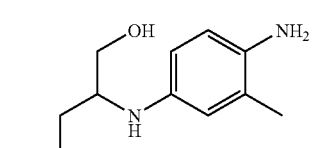 2-(4-amino-3-methylphenylamino)-4-methylpentan-1-ol

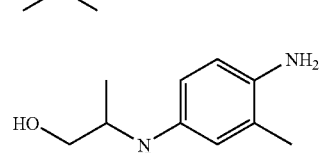 2-(4-amino-3-methylphenylamino)-propan-1-ol

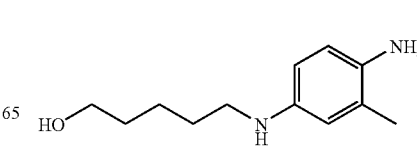 5-(4-amino-3-methylphenylamino)pentan-1-ol

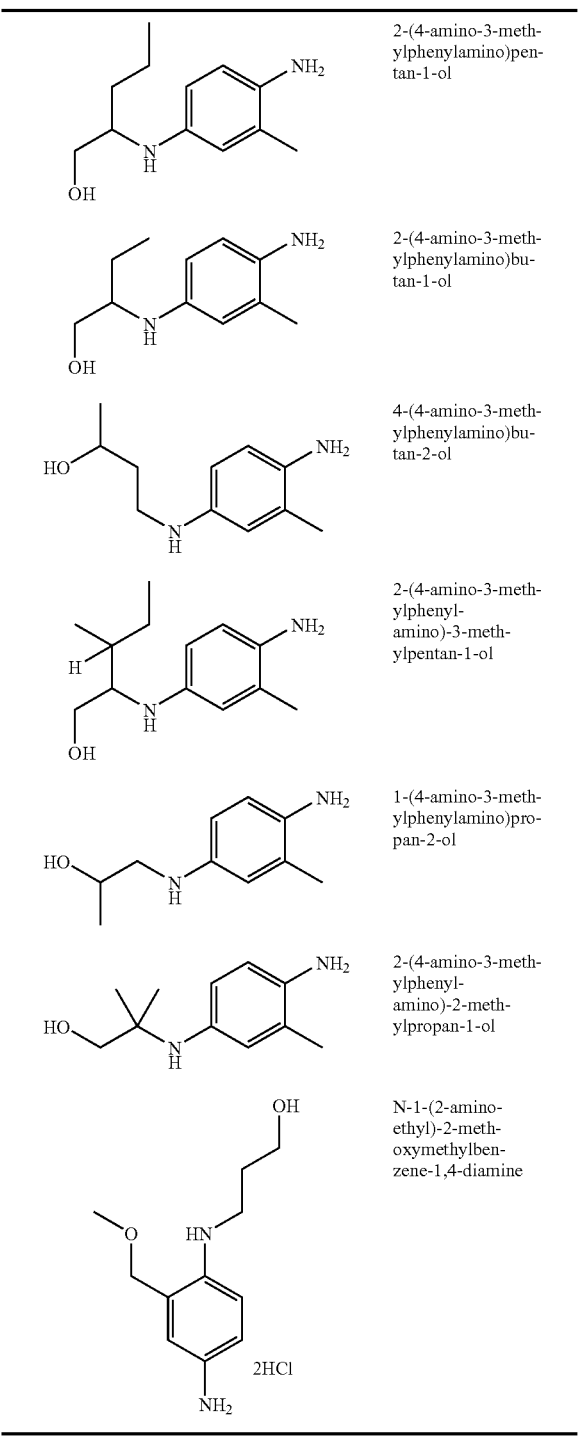

| Structure | Name |
|---|---|
| 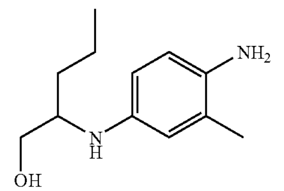 | 2-(4-amino-3-methylphenylamino)pentan-1-ol |
| 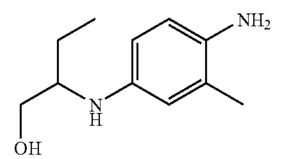 | 2-(4-amino-3-methylphenylamino)butan-1-ol |
| 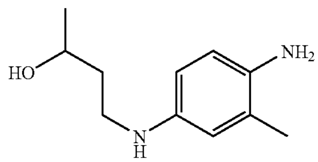 | 4-(4-amino-3-methylphenylamino)butan-2-ol |
| 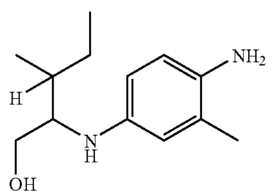 | 2-(4-amino-3-methylphenylamino)-3-methylpentan-1-ol |
| 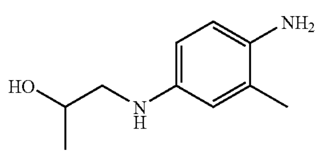 | 1-(4-amino-3-methylphenylamino)propan-2-ol |
| 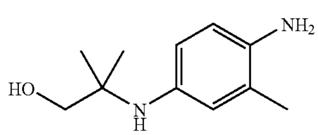 | 2-(4-amino-3-methylphenylamino)-2-methylpropan-1-ol |
| 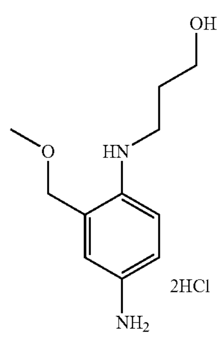 | N-1-(2-aminoethyl)-2-methoxymethylbenzene-1,4-diamine |

The compounds of formula (I) according to the present disclosure may be prepared according to a general method that includes the following: the production of a 4-(N-alkylhydroxy)nitrobenzene compound by nucleophilic substitution of a halogen or of a benzyloxy radical with a hydroxylated amine of formula HOR—NH₂ (R being as defined above) in the presence of a base, followed by reduction of the nitro group of the 4-(N-alkylhydroxyl)nitrobenzene compound obtained to obtain the compound of formula (I):

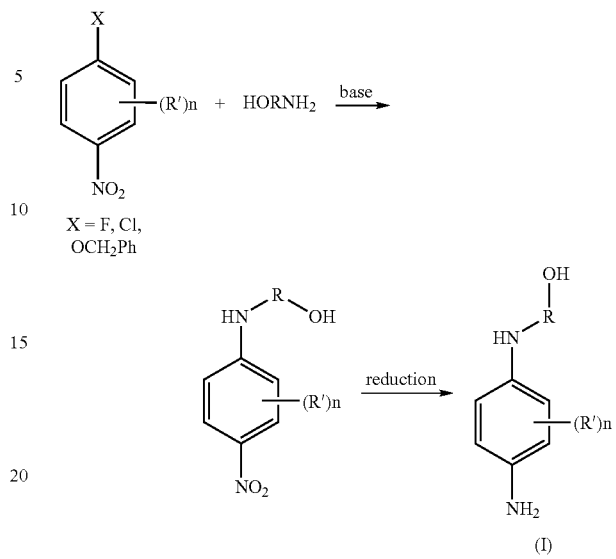

X = F, Cl, OCH₂Ph

The first synthetic part of the process is described in the publications *Synthesis*, 1990 (12), 1147-1148 and *Synth. Commun.*, 1990, 20(22), 3537-3543.

The second part of the process is a standard reduction step, for example by performing a hydrogenation reaction via heterogeneous catalysis in the presence of Pd/C, Pd(II)/C or Raney Nickel, or alternatively by performing a reduction reaction with a metal, for example with zinc, iron, tin. See, for example, *Advanced Organic Chemistry*, 4$^{th}$ edition, 1992, J. March, Wiley Interscience; and *Reduction in Organic Chemistry*, M. Hudlicky, 1983, Ellis Honwood series Chemical Science.

The present disclosure also relates to the nitro compounds of formula (II) and to processes for preparing the secondary para-phenylenediamine compounds of formula (I), in which a step of reduction of the corresponding nitro compound is performed, wherein the term "corresponding nitro compound" is understood to mean the compound of formula (I) in which the amino group para to the NHROH group is replaced with a nitro group. These corresponding nitro compounds are those of formula (II):

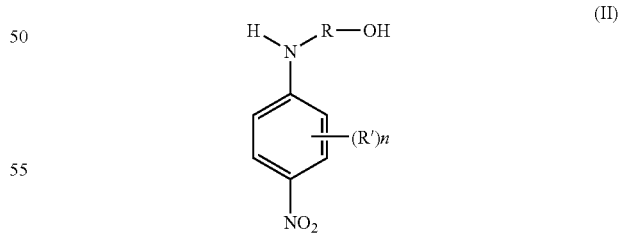

wherein:

R is chosen from linear and branched $C_3$-$C_{10}$ alkylene radicals, optionally substituted with at least one group chosen from amino, monoalkylamino, dialkylamino, alkylcarbonyl, amido, monoalkylaminocarbonyl, and dialkylaminocarbonyl groups, wherein the alkylene radicals are optionally interrupted with at least one heteroatom chosen from nitrogen and oxygen, R' is chosen from alkyl, alkoxy, hydroxyalkoxy, alkoxyalkyl, monohydroxyalkyl and polyhydroxyalkyl radicals, and a chlorine atom, and n is an integer from 1 to 4.

The present disclosure also relates to the uses of the compounds of formula (I) as disclosed herein, for instance the use of the compounds of formula (I) according to the present disclosure for dyeing fibers, for instance keratin fibers such as the hair.

The present disclosure also relates to a cosmetic composition for dyeing fibers, for instance keratin fibers such as the hair, comprising, in a medium that is suitable for dyeing, at least one compound of formula (I).

The at least one compound of formula (I) can be present in an amount, for example, ranging from 0.0001% to 20%, such as from 0.005% to 6% by weight, relative to the total weight of the composition.

The present disclosure also relates to the use of a cosmetic composition comprising, in a medium that is suitable for dyeing, at least one compound of formula (I), for dyeing fibers, for instance keratin fibers such as the hair.

In one embodiment, the medium that is suitable for dyeing can consist of water, or comprise a mixture of water and at least one organic solvent, for instance branched and unbranched $C_1$-$C_4$ lower alcohols, such as ethanol and isopropanol; polyols and polyol ethers, for instance 2-butoxyethanol, propylene glycol, propylene glycol monomethyl ether, diethylene glycol monomethyl ether and monoethyl ether, glycerol, and also aromatic alcohols, for instance benzyl alcohol or phenoxyethanol, and mixtures thereof.

For example, the cosmetic composition can further comprise at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents or opacifiers, vitamins, and provitamins. The at least one adjuvant, when present in the composition, can be present in an amount for each adjuvant ranging from 0.01% to 20% by weight, relative to the weight of the composition.

The composition according to the present disclosure can also comprise, for instance, at least one additional oxidation dye precursor other than the compounds of formula (I), and for further example, the composition as disclosed herein can also comprise at least one coupler.

Among the oxidation couplers that may be used as disclosed herein, non-limiting mention may be made of meta-phenylenediamines, meta-aminophenols, meta-diphenols, naphthalene-based couplers, heterocyclic couplers, and the addition salts thereof. Further non-limiting examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene (or resorcinol), 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the addition salts thereof.

The at least one oxidation coupler, when it is present, can be present in an amount ranging from 0.0001% to 20%, for instance ranging from 0.005% to 6% by weight, relative to the total weight of the composition.

The additional oxidation bases other than the compounds of formula (I) may be chosen from, by way of non-limiting example, para-phenylenediamines, bis(phenyl)alkylenediamines, para-aminophenols, ortho-aminophenols, heterocyclic bases, and the addition salts thereof.

Among the para-phenylenediamines, non-limiting mention may be made, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methyl-aniline, N,N-bis(β-hydroxyethyl)-para-phenylenediamine, 4-amino-2-methyl-N,N-bis(β-hydroxyethyl)aniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-α-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, 6-(4-aminophenylamino)hexan-1-ol, and the acid addition salts thereof.

Among the para-phenylenediamines mentioned above, further non-limiting mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Among the bis(phenyl)alkylenediamines that may be used, non-limiting mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)
ethylenediamine, 1,8-bis(2,5-diaminophenoxy)-3,6-dioxaoctane, and the acid addition salts thereof.

Among the para-aminophenols that may be used, mention may be made, by way of non-limiting example, of para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6 [((5'-amino-2'-hydroxy-3'-methyl)phenyl)methyl]2-methylphenol, bis(5'-amino-2'-hydroxy)phenylmethane, and the acid addition salts thereof.

Among the ortho-aminophenols that may be used, mention may be made, by way of non-limiting example, of 2-aminophenol, 2-amino-5-methylphenol, 2-amino-6-methylphenol, 5-acetamido-2-aminophenol, and the acid addition salts thereof.

Among the heterocyclic bases that may be used, mention may be made, by way of non-limiting example, of pyridine derivatives, pyrimidine derivatives and pyrazole derivatives.

Among the pyridine derivatives, non-limiting mention may be made of the compounds described, for example, in British Patent Nos. GB 1 026 978 and GB 1 153 196, such as 2,5-diaminopyridine, 2-(4-methoxyphenyl)amino-3-aminopyridine, 3,4-diaminopyridine, and the acid addition salts thereof.

Other non-limiting examples of pyridine oxidation bases that are useful in the composition of the present disclosure include the 3-aminopyrazolo[1,5-a]pyridine oxidation bases and the addition salts thereof described, for example, in French Patent Application No. FR 2 801 308. Further non-limiting examples that may be mentioned include pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridin-2-carboxylic acid; 2-methoxypyrazolo[1,5-a]pyrid-3-ylamine; (3-aminopyrazolo[1,5-a]pyrid-5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyridine-3-ylamine; pyrazolo[1,5-a]pyrid-3,5-diamine; 5-morpholin-4-ylpyrazolo[1,5-a]pyrid-3-ylamine; 2-[(3-aminopyrazolo[1,5-a]pyrid-5-yl)-(2-hydroxyethyl)amino]ethanol; 2-[(3-aminopyrazolo[1,5-a]pyrid-7-yl)-(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyridine-6-ol; 3-aminopyrazolo[1,5-a]pyrid-7-ol; and also the acid addition salts thereof.

Among the pyrimidine derivatives that may be used, non-limiting mention may be made of the compounds described, for example, in German Patent No. DE 2 359 399; Japanese Patent Nos. JP 88 169 571 and JP 05 63 124; European Patent No. EP 0 770 375, and International Patent Application No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be used, non-limiting mention may be made of the compounds described in German Patent Nos. DE 3 843 892 and DE 4 133 957, International Patent Application Nos. WO 94/08969 and WO 94/08970, French Patent Application No. FR-A-2 733 749, and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

The at least one oxidation base other than those of formula (I), when present, can be present in an amount ranging from 0.0001% to 20%, such as ranging from 0.005% to 6% by weight, relative to the total weight of the composition.

For example, the addition salts with an acid that can be used for the oxidation bases and the couplers can be chosen from, for instance, the hydrochlorides, hydrobromides, sulfates, citrates, succinates, tartrates, lactates, tosylates, benzenesulfonates, phosphates and acetates.

The dye composition in accordance with the present disclosure may also comprise at least one direct dye, which can be chosen from, for instance, neutral, acidic and cationic nitrobenzene dyes; neutral, acidic and cationic azo direct dyes; neutral, acidic and cationic quinone, such as anthraquinone direct dyes; azine direct dyes; methine, azomethine, triarylmethane and indoamine direct dyes; and natural direct dyes. For example, the composition according to the present disclosure may comprise at least one dye chosen from cationic direct dyes and natural direct dyes.

Among the cationic direct dyes that may be used according to the present disclosure, non-limiting mention may be made of the cationic azo direct dyes described in International Patent Application Nos. WO 95/15144 and WO 95/01772, and European Patent Application No. EP 714 954. Among these compounds, mention may be made, by way of non-limiting example, of the following dyes:

1,3-dimethyl-2-[[4-(dimethylamino)phenyl]azo]1H-imidazolium chloride, 1,3-dimethyl-2-[(4-aminophenyl)azo]1H-imidazolium chloride, and 1-methyl-4-[(methylphenylhydrazono)methyl]pyridinium methyl sulfate.

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin, and apigenidin. It is also possible to use extracts or decoctions comprising these natural dyes, such as henna-based poultices or extracts.

The at least one direct dye, when present in the composition, can be present in an amount ranging from 0.001% to 20% by weight, for instance from 0.005% to 10% by weight, relative to the total weight of the composition.

Needless to say, a person skilled in the art will take care to select the adjuvant(s), additional oxidation dye precursor(s) and direct dye(s) such that the beneficial properties intrinsically associated with the oxidation dye composition in accordance with the present disclosure are not, or are not substantially, adversely affected by the envisaged addition(s).

The pH of the dye composition in accordance with the present disclosure can range from 3 to 12, such as from 5 to 11. It may be adjusted to the desired value using acidifying or basifying agents usually used in the dyeing of keratin fibers, or alternatively using standard buffer systems.

Among the acidifying agents that may be used, non-limiting mention may be made of, for example, mineral or organic acids other than carboxylic diacids, for instance hydrochloric acid, orthophosphoric acid, sulfuric acid, carboxylic acids, for instance acetic acid, tartaric acid, citric acid and lactic acid, and sulfonic acids.

Among the basifying agents that may be used, non-limiting mention may be made of, for example, aqueous ammonia, alkali metal carbonates, alkanolamines such as monoethanolamine, diethanolamine and triethanolamine and also derivatives thereof, sodium hydroxide, potassium hydroxide and the compounds of formula:

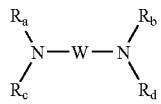

wherein W is a propylene residue optionally substituted with a hydroxyl group or a $C_1$-$C_4$ alkyl radical; $R_a$, $R_b$, $R_c$ and $R_d$, which may be identical or different, are chosen from hydrogen atoms and $C_1$-$C_4$ alkyl and $C_1$-$C_4$ hydroxyalkyl radicals.

The cosmetic composition according to the present disclosure may be in various forms, such as in the form of liquids, creams or gels, or in any other form that is suitable for dyeing keratin fibers, such as human hair.

The present disclosure also relates to a process for dyeing keratin fibers in which the dye composition as defined above is applied to the keratin fibers and left for a period of time that is sufficient to develop the desired coloration, in the presence of an oxidizing agent, wherein the oxidizing agent can be applied before, simultaneously with or after the dye composition. The color may be developed at acidic, neutral or alkaline pH and the oxidizing agent may be added to the composition of the present disclosure just at the time of use, or it may be used as an oxidizing composition comprising it, which can be applied simultaneously with or sequentially to the dye composition as disclosed herein.

According to one embodiment of the present disclosure, the dye composition as disclosed herein is mixed, for instance, at the time of use, with a composition comprising, in a medium that is suitable for dyeing, at least one oxidizing agent, wherein the at least one oxidizing agent is present in an amount that is sufficient to develop a coloration. According to this embodiment, a "ready-to-use" composition is provided, which is a mixture of a dye composition as disclosed herein with at least one oxidizing agent chosen from, for instance, hydrogen peroxide, urea peroxide, alkali metal bromates, persalts, peracids and oxidase enzymes. The mixture obtained, in the form of a ready-to-use composition, is then applied to the keratin fibers for a period of time that is sufficient to develop the desired coloration. After a period of action time ranging from 3 to 50 minutes, such as from 5 to 30 minutes, the keratin fibers are rinsed, washed with a shampoo, rinsed again and then dried.

The oxidizing agents conventionally used for the oxidation dyeing of keratin fibers include, for example, hydrogen peroxide, urea peroxide, alkali metal bromates, persalts such as perborates and persulfates, peracids and oxidase enzymes, among which non-limiting mention may be made of peroxidases, two-electron oxidoreductases such as uricases, and four-electron oxygenases, for instance laccases. In one embodiment of the present disclosure, hydrogen peroxide is used as the oxidizing agent.

The oxidizing composition may also comprise at least one adjuvant conventionally used in hair dye compositions and as defined above.

The pH of the oxidizing composition comprising the oxidizing agent is such that, after mixing with the dye composition, the pH of the resulting composition applied to the keratin fibers ranges, for example, from 3 and 12, such as from 5 to 11. It may be adjusted to the desired value by means of acidifying or basifying agents usually used in the dyeing of keratin fibers and as defined above.

The ready-to-use composition that is applied to the keratin fibers may be in various forms, such as in the form of liquids, creams or gels, or in any other form that is suitable for dyeing keratin fibers, such as human hair.

Another aspect of the present disclosure is a multi-compartment device or dyeing "kit," in which at least one first compartment comprises at least one dye composition as defined above, and at least one second compartment comprises at least one oxidizing composition. This kit may be equipped with a device for applying the desired mixture to the hair, such as the devices described in French Patent No. FR 2 586 913.

Using this kit, it is possible to dye keratin fibers via a process that includes mixing at least one dye composition in accordance with the present disclosure with at least one oxidizing agent as defined above, and applying the mixture obtained to the keratin fibers for a period of time that is sufficient to develop the desired coloration.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The examples that follow serve to illustrate the invention without, however, being limiting in nature.

SYNTHESIS EXAMPLES

Example 1

Synthesis of N-1-(2-aminoethyl)-2-methoxymethyl-benzene-1,4-diamine dihydrochloride (4)

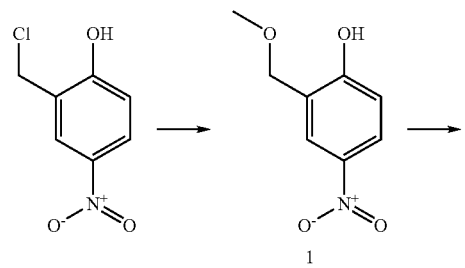

1

-continued

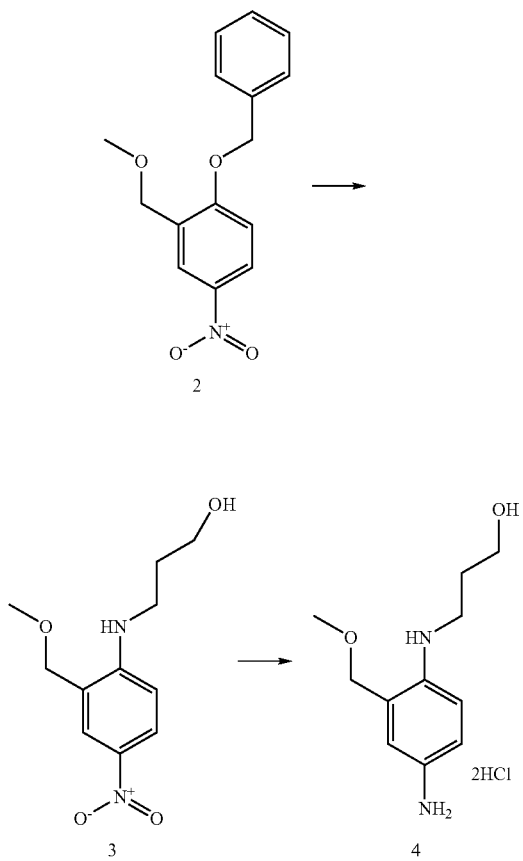

Step 1: Preparation of 2-methoxymethyl-4-nitrophenol (1)

18.7 g (0.1 mol) of 2-chloromethyl-4-nitrophenol and 50 ml of pure methanol were mixed together and refluxed for 2 hours 30 minutes. 37 ml of sodium methoxide (0.2 mol, 5.4 N solution in MeOH) were added and the mixture was refluxed for another 30 minutes. The resulting mixture was cooled in an ice bath and diluted with 350 ml of water, and the insoluble matter formed was filtered off. The filtrate was acidified with acetic acid (10 ml). The crystalline product was filtered off by suction, reslurried in ice-cold water and then dried over $P_2O_5$ at 40° C. 11.4 g of crude products were isolated and then recrystallized from 15 ml of isopropyl acetate to give 7.5 g of expected product.

Step 2: Preparation of 1-benzyloxy-2-methoxymethyl-4-nitrobenzene (2)

18.3 g of 2-methoxymethyl-4-nitrophenol (1) (0.1 mol), 8.3 g (0.06 mol) of potassium carbonate and 40 ml of dimethylformamide were heated on a boiling water bath, and 12.1 ml (0.105 mol) of benzyl chloride were added over 10 minutes. After heating for 1 hour on the boiling water bath, the mixture was poured onto 150 g of ice. The yellow-brown crystals formed were filtered off, reslurried in ice-cold water and washed with petroleum ether. The wet product was recrystallized from 75 ml of isopropanol to give, after drying, 21 g of expected product with a melting point of 108° C. The results of the elementary analyses were as follows:

|   | THEORY | FOUND |
|---|--------|-------|
| C | 65.93  | 65.86 |
| H | 5.53   | 5.56  |
| N | 5.13   | 5.19  |
| O | 23.42  | 23.62 |

Step 3: Preparation of 2-(2-methoxymethyl-4-nitrophenylamino)ethanol (3)

13.6 g (0.05 mol) of 1-benzyloxy-2-methoxymethyl-4-nitrobenzene (2) and 30 ml of 3-aminopropanol were heated at 150-160° C. for 1 hour. The mixture was poured onto ice and the excess 3-aminopropanol was neutralized with 36% hydrochloric acid. The oil formed was separated out by settling of the phases and then crystallized. After filtering off by suction, the crystals were washed with water and then with petroleum ether. Drying under vacuum over $P_2O_5$ at 30° C. gave an orange oil (7.2 g) that crystallized at 20° C.

Step 4: Preparation of 2-(4-amino-2-methoxymethylphenylamino)ethanol, dihydrochloride (4)

A mixture of zinc powder (14 g) ammonium chloride (0.56 g), water (2.8 ml) and 96% ethanol (28 ml) was refluxed on a boiling water bath. The nitro derivative 2-(2-methoxymethyl-4-nitrophenylamino)ethanol (3) (6.8 g, 0.028 mol) was added portion-wise and heating was continued until the reaction medium had decolorized. The mixture was filtered while boiling and the filtrate was recovered onto 12 ml of 6 N hydrochloric ethanol. After evaporating to dryness, the crude product was taken up in 10 ml of absolute ethanol. The crystals formed were filtered off by suction and dried under vacuum over $P_2O_5$/KOH to give 5.6 g of dihydrochloride product.

The proton NMR and mass spectra were in accordance with the expected structure of the product.

Example 2

Synthesis of 2-[2-(4-amino-2-methylphenylamino)ethylamino]ethanol dihydrochloride (6)

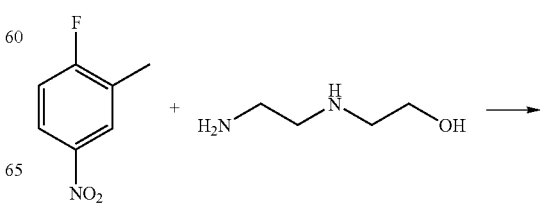

-continued

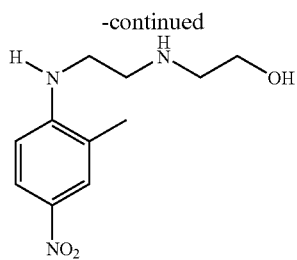

5

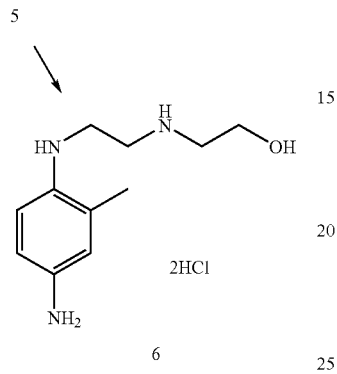

6

Step 1: Synthesis of 2-[2-(4-nitro-2-methylphenylamino)ethylamino]ethanol (5)

2 g of 4-fluoro-3-methyl nitrobenzene, 1.61 g of 2-(2-aminoethylamino)ethanol and 2.14 g of $K_2CO_3$ were added to a solution of 20 ml of N-methylpyrrolidinone. The reaction medium was heated at 60° C. for 7 hours and, after cooling to room temperature, was then poured into a water and ice mixture. The yellow precipitate formed was filtered off, reslurried in water and then dried over $P_2O_5$. 2.4 g of 2-[2-(4-nitro-2-methylphenylamino)ethylamino]ethanol (5) were obtained.

Step 2: Synthesis of 2-[2-(4-amino-2-methylphenylamino)ethylamino]ethanol dihydrochloride (6)

The 2-[2-(4-nitro-2-methylphenylamino)ethylamino]ethanol (5) obtained above was reduced with a boiling zinc/ammonium chloride/water/ethanol mixture. The corresponding amine was isolated in dihydrochloride form.

The proton NMR and mass spectra were in accordance with the expected structure of the product.

Example 3

Synthesis of 2-[2-(4-amino-3-methylphenylamino)ethylamino]ethanol dihydrochloride (8)

-continued

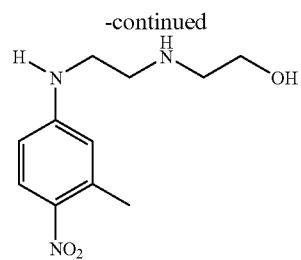

7

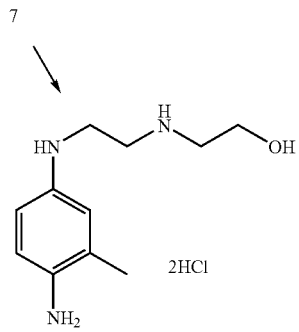

8

Step 1: Synthesis of 2-[2-(4-nitro-3-methylphenylamino)ethylamino]ethanol (7)

2 g of 4-fluoro-2-methyl-nitrobenzene, 1.61 g of 2-(2-aminoethylamino)ethanol and 2.14 g of $K_2CO_3$ were added to a solution of 20 ml of N-methylpyrrolidinone. The reaction medium was heated at 60° C. for 7 hours and, after cooling to room temperature, was then poured into a water and ice mixture. The yellow precipitate formed was filtered off, reslurried in water and then dried over $P_2O_5$. 1.3 g of 2-[2-(4-nitro-3-methylphenylamino)ethylamino]ethanol (7) were obtained.

Step 2: Synthesis of 2-[2-(4-amino-3-methylphenylamino)ethylamino]ethanol dihydrochloride (8)

The 2-[2-(4-nitro-3-methylphenylamino)ethylamino]ethanol (7) obtained above was reduced with a boiling zinc/ammonium chloride/water/ethanol mixture. The corresponding amine was isolated in dihydrochloride form.

The proton NMR and mass spectra were in accordance with the expected structure of the product.

Example 4

Synthesis of 6-(4-amino-3-methylphenylamino)hexan-1-ol dihydrochloride (10)

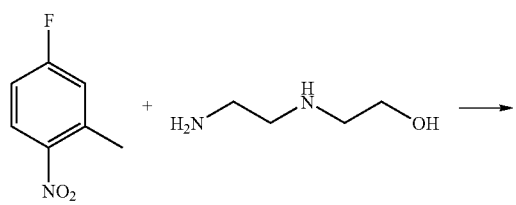

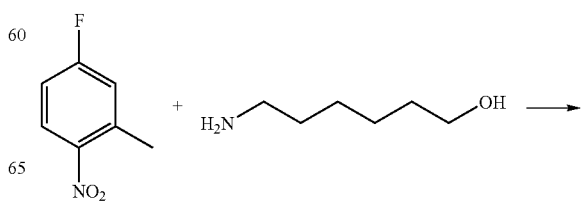

-continued

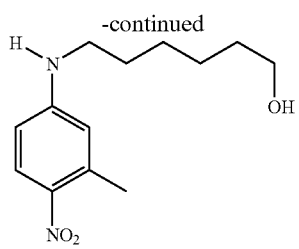

9

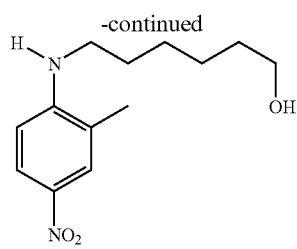

11

↓

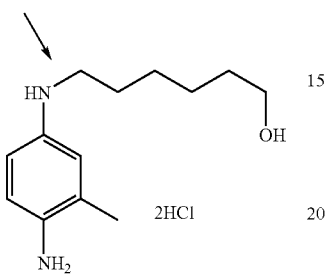

10

↓

12

Step 1: Synthesis of 6-(4-nitro-3-methylphenylamino)hexan-1-ol (9)

10 g of 4-fluoro-2-methylnitrobenzene, 9.97 g of 6-amino-1-capronol and 11.76 g of $K_2CO_3$ were added to a solution of 100 ml of N-methylpyrrolidinone. The reaction medium was heated at 70° C. for 8 hours and, after cooling to room temperature, was then poured into water. The aqueous phase was extracted with ethyl acetate and the organic phase was then dried over $MgSO_4$ and evaporated to dryness to obtain an oil. This oil was purified by chromatography on a column of silica (eluent: heptane/ethyl acetate). 17.8 g of 6-(4-nitro-3-methylphenylamino)hexan-1-ol (9) were obtained in the form of a yellow solid.

Step 2: Synthesis of 6-(4-amino-3-methylphenylamino)hexan-1-ol dihydrochloride (10)

The 6-(4-nitro-3-methylphenylamino)hexan-1-ol (9) obtained above was reduced with a boiling zinc/ammonium chloride/water/ethanol mixture. The corresponding amine was isolated in dihydrochloride form.

The proton NMR and mass spectra were in accordance with the expected structure of the product.

Example 5

Synthesis of 6-(4-amino-2-methylphenylamino)hexan-1-ol dihydrochloride (12)

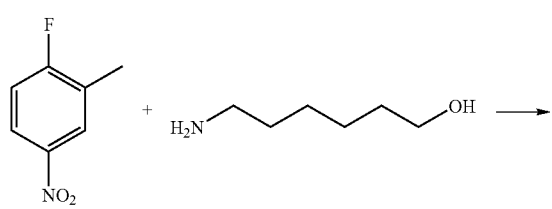

Step 1: Synthesis of 6-(4-nitro-2-methylphenylamino)hexan-1-ol (11)

5 g of 4-fluoro-3-methylnitrobenzene, 4.53 g of 6-amino-1-capronol and 5.35 g of $K_2CO_3$ were added to a solution of 50 ml of N-methylpyrrolidinone. The reaction medium was heated at 70° C. for 7 hours and, after cooling to room temperature, was then poured into a water and ice mixture. The yellow precipitate formed was filtered off, reslurried in water and then dried over $P_2O_5$. 5.9 g of 6-(4-nitro-2-methylphenylamino)hexan-1-ol (11) were obtained.

Step 2: Synthesis of 6-(4-amino-2-methylphenylamino)hexan-1-ol dihydrochloride (12)

The 6-(4-nitro-2-methylphenylamino)hexan-1-ol (11) obtained above was reduced with a boiling zinc/ammonium chloride/water/ethanol mixture. The corresponding amine was isolated in dihydrochloride form.

The proton NMR and mass spectra were in accordance with the expected structure of the product.

Example 6

Synthesis of 2-[2-(4-amino-2-methylphenylamino)ethoxy]ethanol dihydrochloride (14)

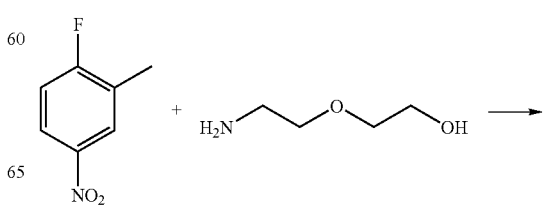

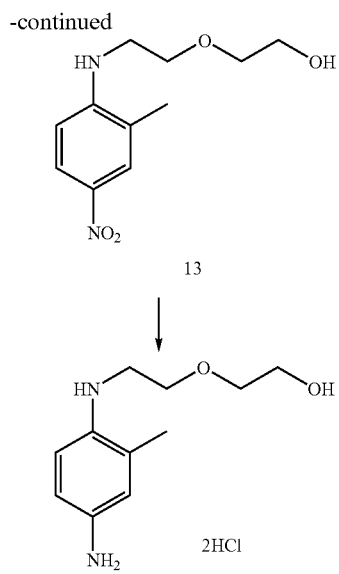

13

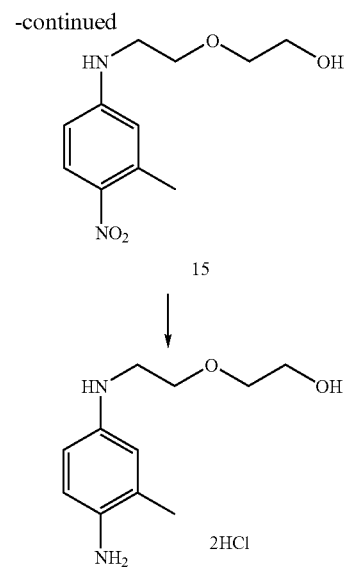

15

Step 1: Synthesis of 2-[2-(4-nitro-2-methylphenylamino)ethoxy]ethanol (13)

2 g of 2-fluoro-5-nitrotoluene were added to a solution of 20 ml of N-methylpyrrolidinone, 1.63 g of 2-aminoethoxyethanol and 2.14 g of $K_2CO_3$. The reaction medium was heated at 60° C. for 12 hours and, after cooling to room temperature, was then poured into a water and ice mixture. The resulting medium was extracted with ethyl acetate and the organic phase was then concentrated under vacuum. 2.2 g of 2-[2-(4-nitro-2-methylphenylamino)ethoxy]ethanol (13) were obtained.

Step 2: Synthesis of 2-[2-(4-amino-2-methylphenylamino)ethoxy]ethanol dihydrochloride (14)

The 2-[2-(4-nitro-2-methylphenylamino)ethoxy]ethanol (13) obtained above was reduced with a boiling zinc/ammonium chloride/water/ethanol mixture. The corresponding amine was isolated in dihydrochloride form.

The proton NMR and mass spectra were in accordance with the expected structure of the product.

Example 7

Synthesis of 2-[2-(4-amino-3-methylphenylamino)ethoxy]ethanol dihydrochloride (16)

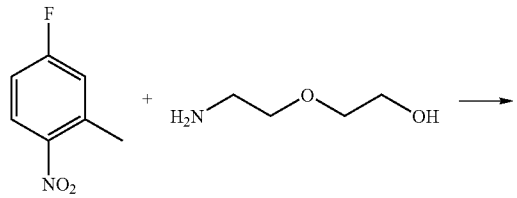

Step 1: Synthesis of 2-[2-(4-nitro-3-methylphenylamino)ethoxy]ethanol (15)

2 g of 5-fluoro-2-nitrotoluene were added to a solution of 20 ml of N-methylpyrrolidinone, 1.63 g of 2-aminoethoxyethanol and 2.14 g of $K_2CO_3$. The reaction medium was heated at 60° C. for 12 hours and, after cooling to room temperature, was then poured into a water and ice mixture. The yellow precipitate formed was filtered off, reslurried in water and then dried over $P_2O_5$. 1.9 g of 2-[2-(4-nitro-3-methylphenylamino)ethoxy]ethanol (15) were obtained after purification on a column of silica.

Step 2: Synthesis of 2-[2-(4-amino-3-methylphenylamino)ethoxy]ethanol dihydrochloride (16)

The 2-[2-(4-nitro-2-methylphenylamino)ethoxy]ethanol (15) obtained above was reduced with a boiling zinc/ammonium chloride/water/ethanol mixture. The corresponding amine was isolated in dihydrochloride form.

The proton NMR and mass spectra were in accordance with the expected structure of the product.

Example 8

Synthesis of 5-(4-amino-3-methylphenylamino)pentan-1-ol dihydrochloride (18)

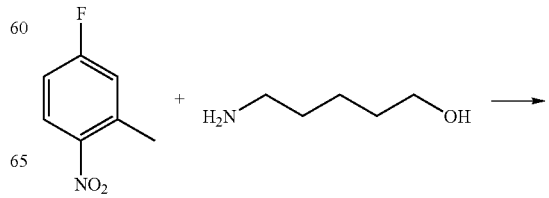

-continued

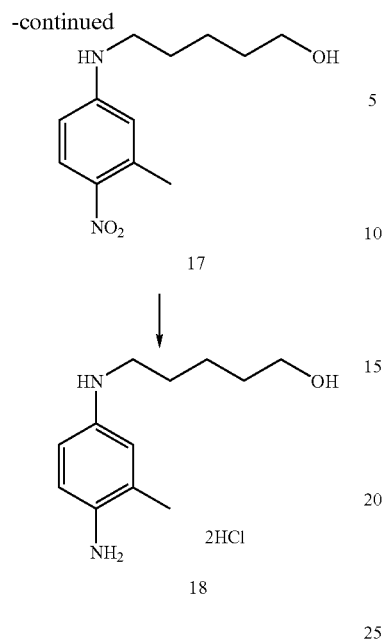

17

↓

18 · 2HCl

Step 1: Synthesis of 5-(4-nitro-3-methylphenylamino)pentan-1-ol (17)

2 g of 5-fluoro-2-nitrotoluene were added to a solution of 20 ml of N-methylpyrrolidinone, 1.6 g of 5-amino-1-pentanol and 2.14 g of $K_2CO_3$. The reaction medium was heated at 60° C. for 8 hours and, after cooling to room temperature, was then poured into a water and ice mixture. The yellow precipitate formed was filtered off, reslurried in water and then dried over $P_2O_5$. 2.38 g of 5-(4-nitro-3-methylphenylamino)pentan-1-ol (17) were obtained.

Step 2: Synthesis of 5-(4-amino-3-methylphenylamino)pentan-1-ol dihydrochloride (18)

The 5-(4-nitro-3-methylphenylamino)pentan-1-ol (17) obtained above was reduced with a boiling zinc/ammonium chloride/water/ethanol mixture. The corresponding amine was isolated in dihydrochloride form.

The proton NMR and mass spectra were in accordance with the expected structure of the product.

Example 9

Synthesis of 5-(4-amino-2-methylphenylamino)pentan-1-ol dihydrochloride (20)

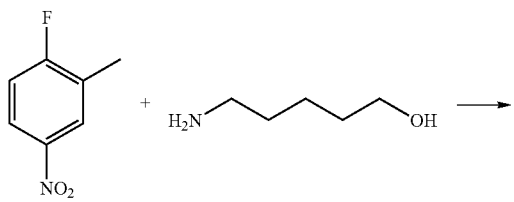

-continued

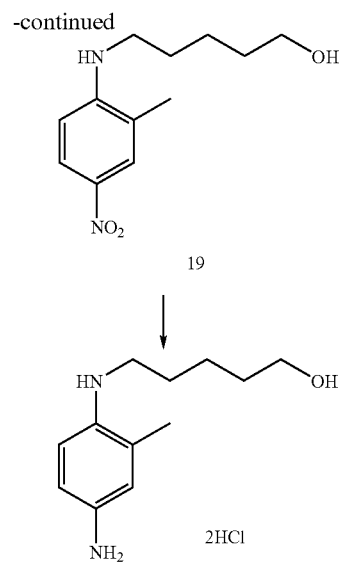

19

↓

20 · 2HCl

Step 1: Synthesis of 5-(4-nitro-2-methylphenylamino)pentan-1-ol (19)

2 g of 2-fluoro-5-nitrotoluene were added to a solution of 20 ml of N-methylpyrrolidinone, 1.6 g of 5-amino-1-pentanol and 2.14 g of $K_2CO_3$. The reaction medium was heated at 60° C. for 12 hours and, after cooling to room temperature, was then poured into a water and ice mixture. The yellow precipitate formed was filtered off, reslurried in water and then dried over $P_2O_5$. 2.9 g of 5-(4-nitro-2-methylphenylamino)pentan-1-ol (19) were obtained.

Step 2: Synthesis of 5-(4-amino-2-methylphenylamino)pentan-1-ol dihydrochloride (20)

The 5-(4-nitro-2-methylphenylamino)pentan-1-ol (19) obtained above was reduced with a boiling zinc/ammonium chloride/water/ethanol mixture. The corresponding amine was isolated in dihydrochloride form.

The proton NMR and mass spectra were in accordance with the expected structure of the product.

Example 10

Synthesis of 5-(4-amino-2-methylphenylamino)butan-1-ol dihydrochloride (22)

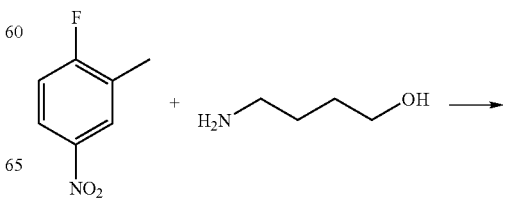

-continued

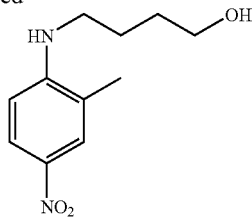

21

↓

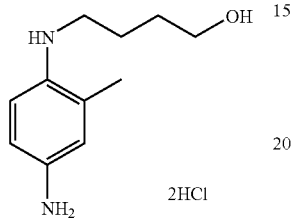

22

Step 1: Synthesis of 5-(4-nitro-2-methylphenylamino)butan-1-ol (21)

2 g of 2-fluoro-5-nitrotoluene, 1.38 g of 4-butanolamine and 2.14 g of $K_2CO_3$ were added to a solution of 20 ml of N-methylpyrrolidinone. The reaction medium was heated at 60° C. for 9 hours and, after cooling to room temperature, was then poured into a water and ice mixture. The yellow precipitate formed was filtered off, reslurried in water and then dried over $P_2O_5$. 2.2 g of 5-(4-nitro-2-methylphenylamino)butan-1-ol (21) were obtained.

Step 2: Synthesis of 5-(4-amino-2-methylphenylamino)butan-1-ol dihydrochloride (22)

The 5-(4-nitro-2-methylphenylamino)butan-1-ol (21) obtained above was reduced with a boiling zinc/ammonium chloride/water/ethanol mixture. The corresponding amine was isolated in dihydrochloride form.

The proton NMR and mass spectra were in accordance with the expected structure of the product.

Example 11

Synthesis of 5-(4-amino-2-methylphenylamino)propan-1-ol dihydrochloride (24)

-continued

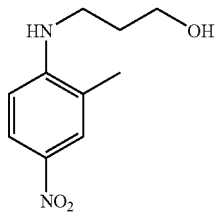

23

↓

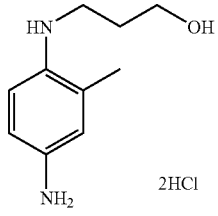

24

Step 1: Synthesis of 5-(4-nitro-2-methylphenylamino)propan-1-ol (23)

2 g of 2-fluoro-5-nitrotoluene were added to a solution of 20 ml of N-methylpyrrolidinone, 1.16 g of N-propanolamine and 2.14 g of $K_2CO_3$. The reaction medium was heated at 60° C. for 12 hours and, after cooling to room temperature, was then poured into a water and ice mixture. The yellow precipitate formed was filtered off, reslurried in water and then dried over $P_2O_5$. 2.15 g of 5-(4-nitro-2-methylphenylamino)propan-1-ol (23) were obtained.

Step 2: Synthesis of 5-(4-amino-2-methylphenylamino)propan-1-ol dihydrochloride (24)

The 5-(4-nitro-2-methylphenylamino)propan-1-ol (23) obtained above was reduced with a boiling zinc/ammonium chloride/water/ethanol mixture. The corresponding amine was isolated in dihydrochloride form.

The proton NMR and mass spectra were in accordance with the expected structure of the product.

Example 12

Synthesis of 3-(4-amino-2-methylphenylamino)-2,2-dimethylpropan-1-ol dihydrochloride (26)

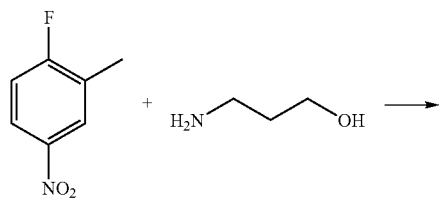

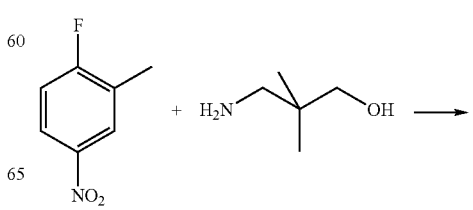

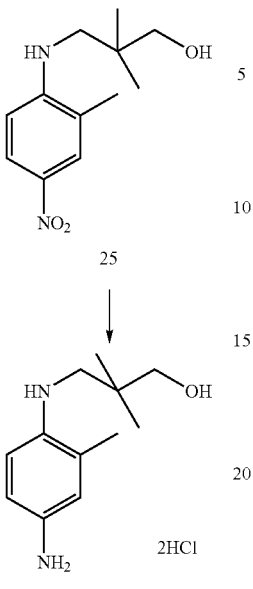

25

26 2HCl

Step 1: Synthesis of 3-(4-nitro-2-methylphenylamino)-2,2-dimethylpropan-1-ol 2 g of 2-fluoro-5-nitrotoluene, 1.59 g of 2,2-dimethyl-3-amino-1-propanol and 2.14 g of $K_2CO_3$ were added to a solution of 20 ml of N-methylpyrrolidinone. The reaction medium was heated at 60° C. for 18 hours and, after cooling to room temperature, was then poured into a water and ice mixture. The yellow precipitate formed was filtered off, reslurried in water and then dried over $P_2O_5$. 1.7 g of 3-(4-nitro-2-methylphenylamino)-2,2-dimethylpropan-1-ol (26) were obtained.

Step 2: Synthesis of 3-(4-amino-2-methylphenylamino)-2,2-dimethylpropan-1-ol dihydrochloride The 3-(4-nitro-2-methylphenylamino)-2,2-dimethylpropan-1-ol (26) obtained above was reduced with a boiling zinc/ammonium chloride/water/ethanol mixture. The corresponding amine was isolated in dihydrochloride form. The proton NMR and mass spectra were in accordance with the expected structure of the product.

Example 13

Synthesis of 4-(4-amino-2-methylphenylamino)butan-2-ol dihydrochloride (28)

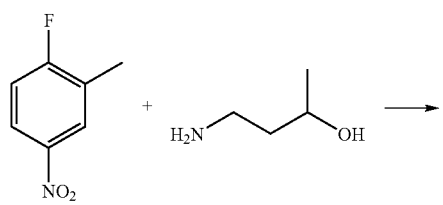

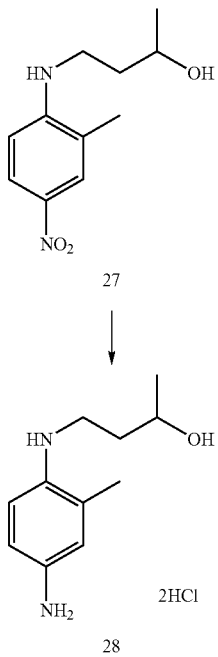

27

28 2HCl

Step 1: Synthesis of 4-(4-nitro-2-methylphenylamino)butan-2-ol (27)

2 g of 2-fluoro-5-nitrotoluene were added to a solution of 20 ml of N-methylpyrrolidinone, 1.38 g of 4-amino-2-butanol and 1.57 g of triethylamine. The reaction medium was heated at 60° C. for 12 hours and, after cooling to room temperature, was then poured into a water and ice mixture. The yellow precipitate formed was filtered off, reslurried in water and then dried over $P_2O_5$. 2.38 g of 4-(4-nitro-2-methylphenylamino)butan-2-ol (27) were obtained.

Step 2: Synthesis of 4-(4-amino-2-methylphenylamino)butan-2-ol dihydrochloride The 4-(4-nitro-2-methylphenylamino)butan-2-ol (27) obtained above was reduced with a boiling zinc/ammonium chloride/water/ethanol mixture. The corresponding amine was isolated in dihydrochloride form.

The proton NMR and mass spectra were in accordance with the expected structure of the product.

Example 14

Synthesis of 5-(4-amino-3-methylphenylamino)butan-1-ol dihydrochloride (30)

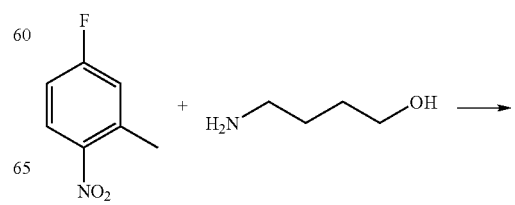

-continued

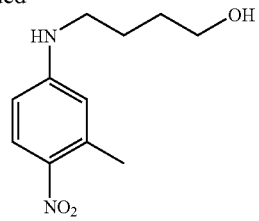

29

↓

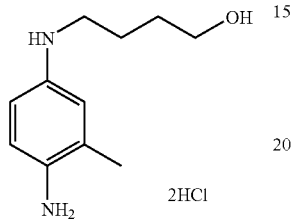

30

Step 1: Synthesis of
5-(4-nitro-2-methylphenylamino)butan-1-ol (29)

2 g of 5-fluoro-2-nitrotoluene were added to a solution of 20 ml of N-methylpyrrolidinone, 1.38 g of 4-amino-1-butanol and 1.57 g of triethylamine. The reaction medium was heated at 60° C. for 12 hours and, after cooling to room temperature, was then poured into a water and ice mixture. The resulting medium was extracted with ethyl acetate and the organic phase was then concentrated under vacuum. 2 g of 5-(4-nitro-2-methylphenylamino)butan-1-ol (29) were obtained.

Step 2: Synthesis of
5-(4-amino-2-methylphenylamino)butan-1-ol
dihydrochloride (30)

The 5-(4-nitro-2-methylphenylamino)butan-1-ol (29) obtained above was reduced with a boiling zinc/ammonium chloride/water/ethanol mixture. The corresponding amine was isolated in dihydrochloride form.
The proton NMR and mass spectra were in accordance with the expected structure of the product.

Example 15

Synthesis of
4-(4-amino-3-methylphenylamino)butan-2-ol
dihydrochloride (32)

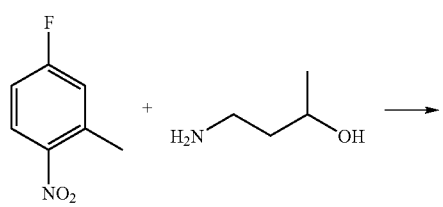

-continued

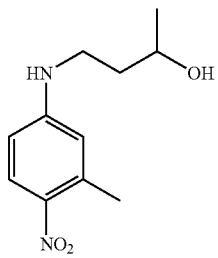

31

↓

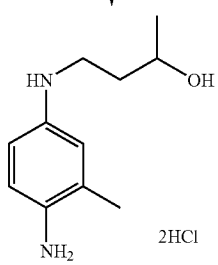

32

Step 1: Synthesis of
4-(4-nitro-3-methylphenylamino)butan-2-ol (31)

2 g of 5-fluoro-2-nitrotoluene were added to a solution of 20 ml of N-methylpyrrolidinone, 1.38 g of 4-amino-2-butanol and 1.57 g of triethylamine. The reaction medium was heated at 60° C. for 10 hours and, after cooling to room temperature, was then poured into a water and ice mixture. The resulting medium was extracted with ethyl acetate and the organic phase was then concentrated under vacuum. 2.88 g of 4-(4-nitro-3-methylphenylamino)butan-2-ol (31) were obtained.

Step 2: Synthesis of
4-(4-amino-3-methylphenylamino)butan-2-ol
dihydrochloride (32)

The 4-(4-nitro-3-methylphenylamino)butan-2-ol (31) obtained above was reduced with a boiling zinc/ammonium chloride/water/ethanol mixture. The corresponding amine was isolated in dihydrochloride form.
The proton NMR and mass spectra were in accordance with the expected structure of the product.

Example 16

Synthesis of
5-(4-amino-3-methylphenylamino)propan-1-ol
dihydrochloride (34)

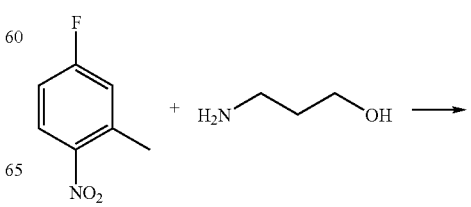

-continued

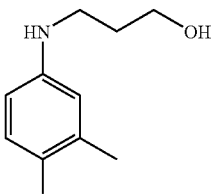

33

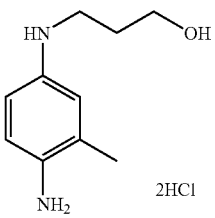

34

Step 1: Synthesis of 5-(4-nitro-3-methylphenylamino)propan-1-ol (33)

2 g of 5-fluoro-2-nitrotoluene were added to a solution of 20 ml of N-methylpyrrolidinone, 1.16 g of N-propanolamine and 2.14 g of $K_2CO_3$. The reaction medium was heated at 60° C. for 12 hours and, after cooling to room temperature, was then poured into a water and ice mixture. The yellow precipitate formed was filtered off, reslurried in water and then dried over $P_2O_5$. 2 g of 5-(4-nitro-3-methylphenylamino)propan-1-ol (33) were obtained.

Step 2: Synthesis of 5-(4-amino-3-methylphenylamino)propan-1-ol dihydrochloride (34)

The 5-(4-nitro-3-methylphenylamino)propan-1-ol (33) obtained above was reduced with a boiling zinc/ammonium chloride/water/ethanol mixture. The corresponding amine was isolated in dihydrochloride form.

The proton NMR and mass spectra were in accordance with the expected structure of the product.

DYEING EXAMPLES

Examples 1 to 3

Dye Compositions Comprising 2-[2-(4-amino-2-methylphenylamino)ethylamino]ethanol dihydrochloride (6)

Examples 1 to 3: Dyeing in Acidic Medium

The following dye compositions were prepared:

|  | Example | | |
|---|---|---|---|
|  | 1 | 2 | 3 |
| 2-[2-(4-Amino-2-methylphenylamino)-ethylamino]ethanol dihydrochloride (6) | $10^{-3}$ mol | $10^{-3}$ mol | $10^{-3}$ mol |
| 5-Amino-2-methylphenol | $10^{-3}$ mol | | |
| 1H-Indol-6-ol | | $10^{-3}$ mol | |
| 2-(2,4-Diaminophenoxy)-ethanol hydrochloride | | | $10^{-3}$ mol |
| Dye support (1) | (*) | (*) | (*) |
| Demineralized water qs | 100 g | 100 g | 100 g |

| (*): dye support (1) pH 7 | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | |
|---|---|---|---|
|  | 1 | 2 | 3 |
| Shade observed | orange | orange | strong brown |

Examples 4 to 15

Dye Compositions Comprising 5-(4-amino-2-methylphenylamino)pentan-1-ol dihydrochloride (20)

Examples 4 to 10: Dyeing in Acidic Medium

The following dye compositions were prepared:

|  | Example | | | | | | |
| --- | --- | --- | --- | --- | --- | --- | --- |
|  | 4 | 5 | 6 | 7 | 8 | 9 | 10 |
| 5-(4-Amino-2-methylphenylamino)pentan-1-ol dihydrochloride (20) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
| --- | --- |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$–$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | | | | | |
| --- | --- | --- | --- | --- | --- | --- | --- |
|  | 4 | 5 | 6 | 7 | 8 | 9 | 10 |
| Shade observed | yellow-brown | strong blue-violet grey | strong grey | strong brown | red | strong blue | strong blue-violet |

Examples 11 to 15: Dyeing in Basic Medium

The following dye compositions were prepared:

|  | Example | | | | |
| --- | --- | --- | --- | --- | --- |
|  | 11 | 12 | 13 | 14 | 15 |
| 5-(4-Amino-2-methylphenylamino)-pentan-1-ol dihydrochloride (20) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 2-Aminopyridin-3-ol | | $10^{-3}$ mol | | | |
| 3,6-Dimethyl-1H-pyrazolo[5,1-c][1,2,4]triazole | | | $10^{-3}$ mol | | |
| 2-(2,4-Diaminophenoxy)-ethanol hydrochloride | | | | $10^{-3}$ mol | |
| 3-Amino-2-chloro-6-methylphenol hydrochloride | | | | | $10^{-3}$ mol |
| Dye support (2) | (*) | (*) | (*) | (*) | (*) |
| Demineralized water qs | 100 g | 100 g | 100 g | 100 g | 100 g |

-continued

| (*): dye support (2) pH 9.5 | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$–$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks are rinsed, washed with a standard shampoo, rinsed again and then dried.

The shades obtained are given in the table below:

| | Example | | | | |
|---|---|---|---|---|---|
| | 11 | 12 | 13 | 14 | 15 |
| Shade observed | strong violet | orange-brown | chromatic red-violet | strong blue | strong blue-violet |

Examples 16 to 26

Dye Compositions Comprising 2-[2-(4-amino-2-methylphenylamino)ethoxy]ethanol dihydrochloride (14)

Examples 16 to 22: Dyeing in Acidic Medium

The following dye compositions were prepared:

| | Example | | | | | | |
|---|---|---|---|---|---|---|---|
| | 16 | 17 | 18 | 19 | 20 | 21 | 22 |
| 2-[2-(4-Amino-2-methylphenylamino)ethoxy]ethanol dihydrochloride (14) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

| (*): dye support (1) pH 7 | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$–$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | | | | | |
|---|---|---|---|---|---|---|---|
|  | 16 | 17 | 18 | 19 | 20 | 21 | 22 |
| Shade observed | yellow-brown | strong violet-grey | orange-brown | red-brown | orange | strong blue | strong blue-violet |

Examples 23 to 26: Dyeing in Basic Medium

The following dye compositions were prepared:

|  | Example | | | |
|---|---|---|---|---|
|  | 23 | 24 | 25 | 26 |
| 2-[2-(4-Amino-2-methyl-phenylamino)ethoxy]ethanol dihydrochloride (14) | $10^{-3}$ mol | $10^{-3}$ mol | $10^{-3}$ mol | $10^{-3}$ mol |
| 5-Amino-2-methylphenol | $10^{-3}$ mol | | | |
| 3,6-Dimethyl-1H-pyrazolo[5,1-c][1,2,4]triazole | | $10^{-3}$ mol | | |
| 2-(2,4-Diaminophenoxy)ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

(*): dye support (2) pH 9.5
| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | | |
|---|---|---|---|---|
|  | 23 | 24 | 25 | 26 |
| Shade observed | red-violet | chromatic red | strong blue | strong blue-violet |

Examples 27 to 30

Dye Compositions Comprising 2-[2-(4-amino-3-methylphenylamino)ethylamino]ethanol dihydrochloride (8)

Examples 27 to 29: Dyeing in Acidic Medium

The following dye compositions were prepared:

|  | Example | | |
|---|---|---|---|
|  | 27 | 28 | 29 |
| 2-[2-(4-Amino-3-methylphenylamino)- | $10^{-3}$ mol | $10^{-3}$ mol | $10^{-3}$ mol |

-continued

| | | | |
|---|---|---|---|
| ethylamino]ethanol dihydrochloride (8) | | | |
| 1H-Indol-6-ol | $10^{-3}$ mol | | |
| 2-(2,4-Diaminophenoxy)-ethanol hydrochloride | | $10^{-3}$ mol | |
| 3-Amino-2-chloro-6-methylphenol hydrochloride | | | $10^{-3}$ mol |
| Dye support (1) | (*) | (*) | (*) |
| Demineralized water qs | 100 g | 100 g | 100 g |

| | |
|---|---|
| (*): dye support (1) pH 7 | |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | |
|---|---|---|---|
| | 27 | 28 | 29 |
| Shade observed | orange | strong blue-green grey | orange-brown |

Example 30: Dyeing in Basic Medium

The following dye composition was prepared:

| | Example 30 |
|---|---|
| 2-[2-(4-Amino-3-methylphenylamino)ethylamino]ethanol dihydrochloride (8) | $10^{-3}$ mol |
| 3-Amino-2-chloro-6-methylphenol hydrochloride | $10^{-3}$ mol |
| Dye support (2) | (*) |
| Demineralized water qs | 100 g |

| | |
|---|---|
| (*): dye support (2) pH 9.5 | |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example 30 |
|---|---|
| Shade observed | red-grey |

Examples 31 to 42

Dye Compositions Comprising 5-(4-amino-2-methylphenylamino)propan-1-ol dihydrochloride (24)

Examples 31 to 37: Dyeing in Acidic Medium

The following dye compositions were prepared:

| | Example | | | | | | |
|---|---|---|---|---|---|---|---|
| | 31 | 32 | 33 | 34 | 35 | 36 | 37 |
| 5-(4-Amino-2-methylphenylamino)propan-1-ol dihydrochloride (24) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4] triazole | | | | | $10^{-3}$ mol | | |
| 2(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

-continued

| | |
|---|---|
| (*): dye support (1) pH 7 | |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$–$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | | | | | |
|---|---|---|---|---|---|---|---|
| | 31 | 32 | 33 | 34 | 35 | 36 | 37 |
| Shade observed | yellow-brown | strong violet-grey | strong grey | strong brown | red | strong blue | strong blue-violet |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained were given in the table below:

| | Example | | | | |
|---|---|---|---|---|---|
| | 38 | 39 | 40 | 41 | 42 |
| Shade observed | violet | orange | chromatic red | strong blue | strong blue-violet |

Examples 38 to 42: Dyeing in Basic Medium

The following dye compositions were prepared:

| | Example | | | | |
|---|---|---|---|---|---|
| | 38 | 39 | 40 | 41 | 42 |
| 5-(4-Amino-2-methylphenylamino)propan-1-ol dihydrochloride (24) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 1H-Indol-6-ol | | $10^{-3}$ mol | | | |
| 3,6-Dimethyl-1H-pyrazolo[5,1-c][1,2,4]triazole | | | $10^{-3}$ mol | | |
| 2-(2,4-Diaminophenoxy)ethanol hydrochloride | | | | $10^{-3}$ mol | |
| 3-Amino-2-chloro-6-methylphenol hydrochloride | | | | | $10^{-3}$ mol |
| Dye support (2) | (*) | (*) | (*) | (*) | (*) |
| Demineralized water qs | 100 g | 100 g | 100 g | 100 g | 100 g |

| | |
|---|---|
| (*): dye support (2) pH 9.5 | |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$–$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

Examples 43 to 55

Dye Compositions Comprising
6-(4-amino-2-methylphenylamino)hexan-1-ol
dihydrochloride (12)

Examples 43 to 49: Dyeing in Acidic Medium

The following dye compositions were prepared:

|  | Example |  |  |  |  |  |  |
| --- | --- | --- | --- | --- | --- | --- | --- |
|  | 43 | 44 | 45 | 46 | 47 | 48 | 49 |
| 6-(4-Amino-2-methylphenylamino)-hexan-1-ol dihydrochloride (12) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol |  |  |  |  |  |  |
| 5-Amino-2-methylphenol |  | $10^{-3}$ mol |  |  |  |  |  |
| 1H-Indol-6-ol |  |  | $10^{-3}$ mol |  |  |  |  |
| 2-Aminopyridin-3-ol |  |  |  | $10^{-3}$ mol |  |  |  |
| 3,6-Dimethyl-1H-pyrazolo[5,1-c][1,2,4]triazole |  |  |  |  | $10^{-3}$ mol |  |  |
| 2-(2,4-Diaminophenoxy)ethanol hydrochloride |  |  |  |  |  | $10^{-3}$ mol |  |
| 3-Amino-2-chloro-6-methylphenol hydrochloride |  |  |  |  |  |  | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| 96° ethyl alcohol | 20.8 g |
| --- | --- |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example |  |  |  |  |  |  |
| --- | --- | --- | --- | --- | --- | --- | --- |
|  | 43 | 44 | 45 | 46 | 47 | 48 | 49 |
| Shade observed | yellow-brown | strong blue-violet | strong grey | strong brown | red | strong blue | strong blue-violet |

Examples 50 to 55: Dyeing in Basic Medium

The following dye compositions were prepared:

|  | Example |  |  |  |  |  |
| --- | --- | --- | --- | --- | --- | --- |
|  | 50 | 51 | 52 | 53 | 54 | 55 |
| 6-(4-Amino-2-methylphenyl-amino)hexan-1-ol dihydrochloride (12) | $10^{-3}$ mol | $10^{-3}$ mol | $10^{-3}$ mol | $10^{-3}$ mol | $10^{-3}$ mol | $10^{-3}$ mol |
| 5-Amino-2-methylphenol | $10^{-3}$ mol |  |  |  |  |  |

-continued

| | | | | | | |
|---|---|---|---|---|---|---|
| 1H-Indol-6-ol | $10^{-3}$ mol | | | | | |
| 2-Aminopyridin-3-ol | | $10^{-3}$ mol | | | | |
| 3,6-Dimethyl-1H-pyrazolo[5,1-c][1,2,4]triazole | | | $10^{-3}$ mol | | | |
| 2-(2,4-Diaminophenoxy)-ethanol hydrochloride | | | | $10^{-3}$ mol | | |
| 3-Amino-2-chloro-6-methylphenol hydrochloride | | | | | $10^{-3}$ mol | |
| Dye support (2) | (*) | (*) | (*) | (*) | (*) | (*) |
| Demineralized water qs | 100 g | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks are rinsed, washed with a standard shampoo, rinsed again and then dried.

The shades obtained are given in the table below:

| | Example | | | | | |
|---|---|---|---|---|---|---|
| | 50 | 51 | 52 | 53 | 54 | 55 |
| Shade observed | strong violet | orange | red-brown | chromatic red-violet | strong blue | strong blue-violet |

Examples 56 to 65

Dye Compositions Comprising 5-(4-amino-3-methylphenylamino)pentan-1-ol dihydrochloride (18)

Examples 55 to 61: Dyeing in Acidic Medium

The following dye compositions were prepared:

| | Example | | | | | |
|---|---|---|---|---|---|---|
| | 56 | 57 | 58 | 59 | 60 | 61 |
| 5-(4-Amino-3-methylphenylamino)pentan-1-ol dihydrochloride (18) | $10^{-3}$ mol | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | | |
| 1H-Indol-6-ol | | $10^{-3}$ mol | | | | |
| 2-Aminopyridin-3-ol | | | $10^{-3}$ mol | | | |
| 3,6-Dimethyl-1H-pyrazolo[5,1-c][1,2,4]triazole | | | | $10^{-3}$ mol | | |
| 2-(2,4-Diaminophenoxy)ethanol hydrochloride | | | | | $10^{-3}$ mol | |
| 3-Amino-2-chloro-6-methylphenol hydrochloride | | | | | | $10^{-3}$ mol |
| Dye support (1) | (*) | (*) | (*) | (*) | (*) | (*) |

|   | -continued |   |   |   |   |   |
|---|---|---|---|---|---|---|
| Demineralized water qs | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | | | | |
|---|---|---|---|---|---|---|
|  | 56 | 57 | 58 | 59 | 60 | 61 |
| Shade observed | strong blue-violet grey | strong red-brown | brown | red | strong blue-green grey | strong blue |

Examples 62 to 65: Dyeing in Basic Medium

The following dye compositions were prepared:

|  | Example | | | |
|---|---|---|---|---|
|  | 62 | 63 | 64 | 65 |
| 5-(4-Amino-3-methylphenylamino)pentan-1-ol dihydrochloride (18) | $10^{-3}$ mol | $10^{-3}$ mol | $10^{-3}$ mol | $10^{-3}$ mol |
| 5-Amino-2-methylphenol | $10^{-3}$ mol | | | |
| 2-Aminopyridin-3-ol | | $10^{-3}$ mol | | |
| 2-(2,4-Diaminophenoxy)ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | | |
|---|---|---|---|---|
|  | 62 | 63 | 64 | 65 |
| Shade observed | strong blue-violet | orange | strong blue-green | strong chromatic blue |

Examples 66 to 78

Dye Compositions Comprising 5-(4-amino-2-methylphenylamino)butan-1-ol dihydrochloride (22)

Examples 66 to 72: Dyeing in Acidic Medium

The following dye compositions were prepared:

|  | Example | | | | | | |
|---|---|---|---|---|---|---|---|
|  | 66 | 67 | 68 | 69 | 70 | 71 | 72 |
| 5-(4-Amino-2-methylphenylamino)butan-1-ol dihydrochloride (22) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | | | | | |
|---|---|---|---|---|---|---|---|
|  | 66 | 67 | 68 | 69 | 70 | 71 | 72 |
| Shade observed | yellow-brown | strong violet | strong grey | strong brown | red | strong blue | strong blue-violet |

Examples 73 to 78: Dyeing in Basic Medium

The following dye compositions were prepared:

|  | Example | | | | | |
|---|---|---|---|---|---|---|
|  | 73 | 74 | 75 | 76 | 77 | 78 |
| 5-(4-Amino-2-methylphenylamino)butan-1-ol dihydrochloride (22) | $10^{-3}$ mol | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | | |

-continued

| | | | | | | |
|---|---|---|---|---|---|---|
| 1H-Indol-6-ol | $10^{-3}$ mol | | | | | |
| 2-Aminopyridin-3-ol | | $10^{-3}$ mol | | | | |
| 3,6-Dimethyl-1H-pyrazolo[5,1-c][1,2,4]triazole | | | $10^{-3}$ mol | | | |
| 2-(2,4-Diaminophenoxy)ethanol hydrochloride | | | | $10^{-3}$ mol | | |
| 3-Amino-2-chloro-6-methylphenol hydrochloride | | | | | $10^{-3}$ mol | |
| Dye support (2) | (*) | (*) | (*) | (*) | (*) | (*) |
| Demineralized water qs | 100 g | 100 g | 100 g | 100 g | 100 g | 100 g |

| | |
|---|---|
| (*): dye support (2) pH 9.5 | |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | | | | |
|---|---|---|---|---|---|---|
| | 73 | 74 | 75 | 76 | 77 | 78 |
| Shade observed | violet | orange | orange-brown | chromatic red | strong blue | strong blue-violet |

Examples 79 to 86

Dye Compositions Comprising 6-(4-Amino-3-methylphenylamino)hexan-1-ol dihydrochloride (10)

Examples 79 to 83: Dyeing in Acidic Medium

The following dye compositions were prepared:

| | Example | | | | |
|---|---|---|---|---|---|
| | 79 | 80 | 81 | 82 | 83 |
| 6-(4-Amino-3-methylphenylamino)hexan-1-ol dihydrochloride (10) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 1H-Indol-6-ol | | $10^{-3}$ mol | | | |
| 2-Aminopyridin-3-ol | | | $10^{-3}$ mol | | |
| 2-(2,4-Diaminophenoxy)ethanol hydrochloride | | | | $10^{-3}$ mol | |
| 3-Amino-2-chloro-6-methylphenol hydrochloride | | | | | $10^{-3}$ mol |
| Dye support (1) | (*) | (*) | (*) | (*) | (*) |
| Demineralized water qs | 100 g | 100 g | 100 g | 100 g | 100 g |

| | |
|---|---|
| (*): dye support (1) pH 7 | |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |

-continued

| | |
|---|---|
| Polyethylene glycol containing 8 ethylene oxide units | 3.0 g |
| Na$_2$HPO$_4$ | 0.28 g |
| KH$_2$PO$_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | | | |
|---|---|---|---|---|---|
| | 79 | 80 | 81 | 82 | 83 |
| Shade observed | strong blue-violet grey | strong brown | brown | strong blue-green grey | strong blue |

Examples 84 to 86: Dyeing in Basic Medium

The following dye compositions were prepared:

| | Example | | |
|---|---|---|---|
| | 84 | 85 | 86 |
| 6-(4-Amino-3-methylphenylamino)hexan-1-ol dihydrochloride (10) | 10$^{-3}$ mol | 10$^{-3}$ mol | 10$^{-3}$ mol |
| 5-Amino-2-methylphenol | 10$^{-3}$ mol | | |
| 2-(2,4-Diaminophenoxy)ethanol hydrochloride | | 10$^{-3}$ mol | |
| 3-Amino-2-chloro-6-methylphenol hydrochloride | | | 10$^{-3}$ mol |
| Dye support (2) | (*) | (*) | (*) |
| Demineralized water qs | 100 g | 100 g | 100 g |

-continued

| | |
|---|---|
| (*): dye support (2) pH 9.5 | |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| C$_8$-C$_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| NH$_4$Cl | 4.32 g |
| Aqueous ammonia containing 20% NH$_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | |
|---|---|---|---|
| | 84 | 85 | 86 |
| Shade observed | strong blue-violet | blue-green | blue |

Examples 87 to 99

Dye Composition Using 4-(4-amino-2-methylphenylamino)butan-2-ol dihydrochloride (28)

Examples 87 to 93: Dyeing in Acidic Medium

The following dye compositions were prepared:

| | Example | | | | | | |
|---|---|---|---|---|---|---|---|
| | 87 | 88 | 89 | 90 | 91 | 92 | 93 |
| 4-(4-Amino-2-methylphenylamino)butan-2-ol dihydrochloride (28) | 10$^{-3}$ mol | 10$^{-3}$ mol | 10$^{-3}$ mol | 10$^{-3}$ mol | 10$^{-3}$ mol | 10$^{-3}$ mol | 10$^{-3}$ mol |
| Benzene-1,3-diol | 10$^{-3}$ mol | | | | | | |
| 5-Amino-2-methylphenol | | 10$^{-3}$ mol | | | | | |
| 1H-Indol-6-ol | | | 10$^{-3}$ mol | | | | |
| 2-Aminopyridin-3-ol | | | | 10$^{-3}$ mol | | | |
| 3,6-Dimethyl-1H-pyrazolo[5,1-c][1,2,4]triazole | | | | | 10$^{-3}$ mol | | |
| 2-(2,4-Diaminophenoxy)ethanol hydrochloride | | | | | | 10$^{-3}$ mol | |
| 3-Amino-2-chloro-6-methylphenol hydrochloride | | | | | | | 10$^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

-continued

| | |
|---|---|
| (*): dye support (1) pH 7 | |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained were given in the table below:

| | Example | | | | | |
|---|---|---|---|---|---|---|
| | 87 | 88 | 89 | 90 | 91 | 92 | 93 |
| Shade observed | yellow-brown | strong violet-grey | strong grey | brown | orange | strong blue | strong blue-violet |

Examples 94 to 99: Dyeing in Basic Medium

The following dye compositions were prepared:

| | Example | | | | | |
|---|---|---|---|---|---|---|
| | 94 | 95 | 96 | 97 | 98 | 99 |
| 4-(4-Amino-2-methylphenylamino)butan-2-ol dihydrochloride (28) | $10^{-3}$ mol | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | | |
| 1H-Indol-6-ol | | $10^{-3}$ mol | | | | |
| 2-Aminopyridin-3-ol | | | $10^{-3}$ mol | | | |
| 3,6-Dimethyl-1H-pyrazolo[5,1-c][1,2,4]triazole | | | | $10^{-3}$ mol | | |
| 2-(2,4-Diaminophenoxy)ethanol hydrochloride | | | | | $10^{-3}$ mol | |
| 3-Amino-2-chloro-6-methylphenol hydrochloride | | | | | | $10^{-3}$ mol |
| Dye support (2) | (*) | (*) | (*) | (*) | (*) | (*) |
| Demineralized water qs | 100 g | 100 g | 100 g | 100 g | 100 g | 100 g |

| | |
|---|---|
| (*): dye support (2) pH 9.5 | |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | | | | |
|---|---|---|---|---|---|---|
| | 94 | 95 | 96 | 97 | 98 | 99 |
| Shade observed | violet | orange | orange | chromatic red | strong blue | strong blue-violet |

Examples 100 to 111

Dye Compositions Comprising 3-(4-amino-2-methylphenylamino)2,2-dimethylpropan-1-ol dihydrochloride (26)

Examples 100 to 106: Dyeing in Acidic Medium

The following dye compositions were prepared:

| | Example | | | | | | |
|---|---|---|---|---|---|---|---|
| | 100 | 101 | 102 | 103 | 104 | 105 | 106 |
| 3-(4-Amino-2-methylphenylamino)2,2-dimethylpropan-1-ol dihydrochloride (26) | $10^{-3}$ mol | $10^{-3}$ mol | $10^{-3}$ mol | $10^{-3}$ mol | $10^{-3}$ mol | $10^{-3}$ mol | $10^{-3}$ mol |
| Benzene-1,3-diol | $10^{-3}$ mol | | | | | | |
| 5-Amino-2-methylphenol | | $10^{-3}$ mol | | | | | |
| 1H-Indol-6-ol | | | $10^{-3}$ mol | | | | |
| 2-Aminopyridin-3-ol | | | | $10^{-3}$ mol | | | |
| 3,6-Dimethyl-1H-pyrazolo[5,1-c][1,2,4]triazole | | | | | $10^{-3}$ mol | | |
| 2-(2,4-Diaminophenoxy)ethanol hydrochloride | | | | | | $10^{-3}$ mol | |
| 3-Amino-2-chloro-6-methylphenol hydrochloride | | | | | | | $10^{-3}$ mol |
| Dye support (1) | (*) | (*) | (*) | (*) | (*) | (*) | (*) |
| Demineralized water qs | 100 g | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | | | | | |
|---|---|---|---|---|---|---|---|
|  | 100 | 101 | 102 | 103 | 104 | 105 | 106 |
| Shade observed | yellow-brown | strong blue-violet | strong red-brown | strong grey | orange-brown | strong blue | strong blue-violet |

Examples 107 to 111: Dyeing in Basic Medium

The following dye compositions were prepared:

|  | Example | | | | |
|---|---|---|---|---|---|
|  | 107 | 108 | 109 | 110 | 111 |
| 3-(4-Amino-2-methylphenylamino) 2,2-dimethylpropan-1-ol dihydrochloride (26) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 2-Aminopyridin-3-ol | | $10^{-3}$ mol | | | |
| 3,6-Dimethyl-1H-pyrazolo[5,1-c][1,2,4]triazole | | | $10^{-3}$ mol | | |
| 2-(2,4-Diaminophenoxy) ethanol hydrochloride | | | | $10^{-3}$ mol | |
| 3-Amino-2-chloro-6-methylphenol hydrochloride | | | | | $10^{-3}$ mol |
| Dye support (2) | (*) | (*) | (*) | (*) | (*) |
| Demineralized water qs | 100 g | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | | | |
| --- | --- | --- | --- | --- | --- |
|  | 107 | 108 | 109 | 110 | 111 |
| Shade observed | violet | red-brown | chromatic red-violet | strong blue | strong blue-violet |

Examples 112 to 119

Dye Compositions Comprising 5-(4-amino-3-methylphenylamino)butan-1-ol dihydrochloride (30)

Examples 112 to 116: Dyeing in Acidic Medium

The following dye compositions were prepared:

|  | Example | | | | |
| --- | --- | --- | --- | --- | --- |
|  | 112 | 113 | 114 | 115 | 116 |
| 5-(4-Amino-3-methylphenylamino)butan-1-ol dihydrochloride (30) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 1H-Indol-6-ol | | $10^{-3}$ mol | | | |
| 2-Aminopyridin-3-ol | | | $10^{-3}$ mol | | |
| 2-(2,4-Diaminophenoxy)ethanol hydrochloride | | | | $10^{-3}$ mol | |
| 3-Amino-2-chloro-6-methylphenol hydrochloride | | | | | $10^{-3}$ mol |
| Dye support (1) | (*) | (*) | (*) | (*) | (*) |
| Demineralized water qs | 100 g | 100 g | 100 g | 100 g | 100 g |

| (*): dye support (1) pH 7 | |
| --- | --- |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

|  | Example | | | | |
| --- | --- | --- | --- | --- | --- |
|  | 112 | 113 | 114 | 115 | 116 |
| Shade observed | strong blue-violet grey | strong red-brown | brown | strong blue-green grey | strong blue |

Examples 117 to 119: Dyeing in Basic Medium

The following dye compositions were prepared:

|  | Example | | |
| --- | --- | --- | --- |
|  | 117 | 118 | 119 |
| 5-(4-Amino-3-methylphenylamino)butan-1-ol dihydrochloride (30) | $10^{-3}$ mol | $10^{-3}$ mol | $10^{-3}$ mol |
| 5-Amino-2-methylphenol | $10^{-3}$ mol | | |
| 2-(2,4-Diaminophenoxy)ethanol hydrochloride | | $10^{-3}$ mol | |
| 3-Amino-2-chloro-6-methylphenol hydrochloride | | | $10^{-3}$ mol |

-continued

| Dye support (2) | (*) | (*) | (*) |
| --- | --- | --- | --- |
| Demineralized water qs | 100 g | 100 g | 100 g |

| (*): dye support (2) pH 9.5 | |
| --- | --- |
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |

-continued

| | |
|---|---|
| Benzyl alcohol | 2.0 g |
| Polyethylene glycol containing 8 ethylene oxide units | 3.0 g |
| NH$_4$Cl | 4.32 g |
| Aqueous ammonia containing 20% NH$_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | |
|---|---|---|---|
| | 117 | 118 | 119 |
| Shade observed | strong blue-violet | strong blue-green | strong chromatic blue |

Examples 120 to 129

Dye Compositions Comprising 2-[2-(4-amino-3-methylphenylamino)ethoxy]ethanol dihydrochloride (16)

Examples 120 to 125: Dyeing in Acidic Medium

The following dye compositions were prepared:

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | | | | |
|---|---|---|---|---|---|---|
| | 120 | 121 | 122 | 123 | 124 | 125 |
| Shade observed | strong violet-grey | orange | orange-brown | orange | strong blue-green grey | strong blue-violet |

| | Example | | | | | |
|---|---|---|---|---|---|---|
| | 120 | 121 | 122 | 123 | 124 | 125 |
| 2-[2-(4-Amino-3-methylphenylamino)ethoxy]ethanol dihydrochloride (16) | 10$^{-3}$ mol | 10$^{-3}$ mol | 10$^{-3}$ mol | 10$^{-3}$ mol | 10$^{-3}$ mol | 10$^{-3}$ mol |
| 5-Amino-2-methylphenol | 10$^{-3}$ mol | | | | | |
| 1H-Indol-6-ol | | 10$^{-3}$ mol | | | | |
| 2-Aminopyridin-3-ol | | | 10$^{-3}$ mol | | | |
| 3,6-Dimethyl-1H-pyrazolo[5,1-c][1,2,4]triazole | | | | 10$^{-3}$ mol | | |
| 2-(2,4-Diaminophenoxy)ethanol hydrochloride | | | | | 10$^{-3}$ mol | |
| 3-Amino-2-chloro-6-methylphenol hydrochloride | | | | | | 10$^{-3}$ mol |
| Dye support (1) | (*) | (*) | (*) | (*) | (*) | (*) |
| Demineralized water qs | 100 g | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| C$_8$-C$_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| Na$_2$HPO$_4$ | 0.28 g |
| KH$_2$PO$_4$ | 0.46 g |

Examples 126 to 129: Dyeing in Basic Medium

The following dye compositions were prepared:

|  | Example | | | |
|---|---|---|---|---|
|  | 126 | 127 | 128 | 129 |
| 2-[2-(4-Amino-3-methylphenylamino)ethoxy]ethanol dihydrochloride (16) | $10^{-3}$ mol | $10^{-3}$ mol | $10^{-3}$ mol | $10^{-3}$ mol |
| 5-Amino-2-methylphenol | $10^{-3}$ mol | | | |
| 3,6-Dimethyl-1H-pyrazolo[5,1-c][1,2,4]triazole | | $10^{-3}$ mol | | |
| 2-(2,4-Diaminophenoxy)ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After an action time of 30 minutes, the locks were rinsed, washed with a standard shampoo, rinsed again and then dried.

The shades obtained are given in the table below:

|  | Example | | | |
|---|---|---|---|---|
|  | 126 | 127 | 128 | 129 |
| Shade observed | violet-grey | chromatic red | blue-green | strong blue |

Examples 130 to 138

Dye Compositions Comprising 4-(4-amino-3-methylphenylamino)butan-2-ol dihydrochloride (32)

Examples 130 to 134: Dyeing in Acidic Medium

The following dye compositions were prepared:

|  | Example | | | | |
|---|---|---|---|---|---|
|  | 130 | 131 | 132 | 133 | 134 |
| 4-(4-Amino-3-methylphenylamino)butan-2-ol dihydrochloride (32) | $10^{-3}$ mol | $10^{-3}$ mol | $10^{-3}$ mol | $10^{-3}$ mol | $10^{-3}$ mol |
| 5-Amino-2-methylphenol | $10^{-3}$ mol | | | | |
| 1H-Indol-6-ol | | $10^{-3}$ mol | | | |
| 2-Aminopyridin-3-ol | | | $10^{-3}$ mol | | |
| 2-(2,4-Diaminophenoxy)ethanol hydrochloride | | | | $10^{-3}$ mol | |
| 3-Amino-2-chloro-6-methylphenol hydrochloride | | | | | $10^{-3}$ mol |
| Dye support (1) | (*) | (*) | (*) | (*) | (*) |

-continued

| | | | | | |
|---|---|---|---|---|---|
| Demineralized water qs | 100 g | 100 g | 100 g | 100 g | 100 g |

(*): dye support (1) pH 7

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ alkyl polyglucoside as an aqueous 60% solution | 3.6 g A.M |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

At the time of use, each composition was mixed with an equal weight of 20-volumes aqueous hydrogen peroxide solution (6% by weight). A final pH of 7 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | | | |
|---|---|---|---|---|---|
| | 130 | 131 | 132 | 133 | 134 |
| Shade observed | strong violet-grey | orange-brown | yellow-brown | strong blue-green grey | strong blue |

Examples 135 to 138: Dyeing in Basic Medium

The following dye compositions were prepared:

| | Example | | | |
|---|---|---|---|---|
| | 135 | 136 | 137 | 138 |
| 4-(4-Amino-3-methylphenylamino)butan-2-ol dihydrochloride (32) | $10^{-3}$ mol | $10^{-3}$ mol | $10^{-3}$ mol | $10^{-3}$ mol |
| 5-Amino-2-methylphenol | $10^{-3}$ mol | | | |
| 3,6-Dimethyl-1H-pyrazolo[5,1-c][1,2,4]triazole | | $10^{-3}$ mol | | |
| 2-(2,4-Diaminophenoxy)ethanol hydrochloride | | | $10^{-3}$ mol | |
| 3-Amino-2-chloro-6-methylphenol hydrochloride | | | | $10^{-3}$ mol |
| Dye support (2) | (*) | (*) | (*) | (*) |
| Demineralized water qs | 100 g | 100 g | 100 g | 100 g |

(*): dye support (2) pH 9.5

| | |
|---|---|
| 96° ethyl alcohol | 20.8 g |
| Sodium metabisulfite as an aqueous 35% solution | 0.23 g A.M |
| Pentasodium salt of diethylenetriaminepentaacetic acid as an aqueous 40% solution | 0.48 g A.M |
| $C_8$-$C_{10}$ Alkyl polyglucoside as an aqueous 60% solution | 3.6 g A.M |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 2.94 g |

At the time of use, each composition was mixed with an equal weight of 20-volumes aqueous hydrogen peroxide solution (6% by weight). A final pH of 9.5 was obtained.

Each mixture obtained was applied to locks of grey hair comprising 90% white hairs. After a period of action time of 30 minutes, the locks were rinsed, washed with a standard shampoo, rinsed again and then dried.

The shades obtained are given in the table below:

| | Example | | | |
|---|---|---|---|---|
| | 135 | 136 | 137 | 138 |
| Shade observed | strong blue-violet grey | chromatic red | strong blue-green | strong blue |

What is claimed is:

1. A compound chosen from ortho-substituted and/or meta-substituted N-alkylhydroxylated secondary para-phenylenediamine compounds of formula (I):

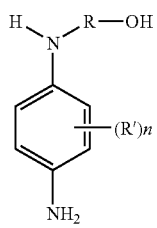

wherein:
R is chosen from linear and branched C₃-C₁₀ alkylene radicals, which are optionally substituted with at least one group chosen from amino, monoalkylamino, dialkylamino, alkylcarbonyl, amido, monoalkylaminocarbonyl and dialkylaminocarbonyl groups, wherein the alkylene radicals are interrupted with at least one heteroatom chosen from nitrogen and oxygen,
R' is chosen from alkyl, alkoxy, hydroxyalkoxy, alkoxyalkyl, monohydroxyalkyl and polyhydroxyalkyl radicals and a chlorine atom, and
n is an integer from 1 to 4.

2. The compound according to claim 1, wherein R is chosen from linear and branched $C_3$-$C_6$alkylene radicals interrupted with a heteroatom chosen from nitrogen and oxygen.

3. The compound according to claim 1, wherein R' is chosen from $C_1$-$C_3$ alkyl and $C_1$-$C_3$ alkoxy groups.

4. The compound according to claim 3, wherein R' is a methyl group.

5. The compound according to claim 1, wherein n is equal to 1 or 2.

6. The compound according to claim 5, wherein n is equal to 1.

7. A compound chosen from:
2-[2-(4-amino-2-methylphenylamino)ethoxy]ethanol;
2-[2-(4-amino-2-methylphenylamino)ethylamino]ethanol;
3-(4-amino-2-methylphenylamino)propan-1-ol;
2-(4-amino-2-methylphenylamino)hexan-1-ol;
1-(4-amino-2-methylphenylamino)butan-2-ol;
3-(4-amino-2-methylphenylamino)2,2-dimethylpropan-1-ol;
6-(4-amino-2-methylphenylamino)hexan-1-ol;
4-(4-amino-2-methylphenylamino)butan-1-ol;
2-(4-amino-2-methylphenylamino)3,3-dimethyl-butan-1-ol;
2-(4-amino-2-methylphenylamino)3-methyl-butan-1-ol;
2-(4-amino-2-methylphenylamino)4-methylpentan-1-ol;
2-(4-amino-2-methylphenylamino)propan-1-ol;
5-(4-amino-2-methylphenylamino)pentan-1-ol;
2-(4-amino-2-methylphenylamino)pentan-1-ol;
2-(4-amino-2-methylphenylamino)butan-1-ol;
4-(4-amino-2-methylphenylamino)butan-2-ol;
2-(4-amino-2-methylphenylamino)3-methylpentan-1-ol;
1-(4-amino-2-methylphenylamino)propan-2-ol;
2-(4-amino-2-methylphenylamino)2-methylpropan-1-ol;
2-[2-(4-amino-3-methylphenylamino)ethoxy]ethanol;
2-[2-(4-amino-3-methylphenylamino)ethylamino]ethanol;
3-(4-amino-3-methylphenylamino)propan-1-ol;
2-(4-amino-3-methylphenylamino)hexan-1-ol;
1-(4-amino-3-methylphenylamino)butan-2-ol;
3-(4-amino-3-methylphenylamino)2,2-dimethylpropan-1-ol;
6-(4-amino-3-methylphenylamino)hexan-1-ol;
4-(4-amino-3-methylphenylamino)butan-1-ol;
2-(4-amino-3-methylphenylamino)3,3-dimethylbutan-1-ol;
2-(4-amino-3-methylphenylamino)3-methylbutan-1-ol;
2-(4-amino-3-methylphenylamino)4-methylpentan-1-ol;
2-(4-amino-3-methylphenylamino)propan-1-ol;
5-(4-amino-3-methylphenylamino)pentan-1-ol;
2-(4-amino-3-methylphenylamino)pentan-1-ol;
2-(4-amino-3-methylphenylamino)butan-1-ol;
4-(4-amino-3-methylphenylamino)butan-2-ol;
2-(4-amino-3-methylphenylamino)3-methylpentan-1-ol;
1-(4-amino-3-methylphenylamino)propan-2-ol;
2-(4-amino-3-methylphenylamino)2-methylpropan-1-ol; and
N-1-(2-aminoethyl)2-methoxymethylbenzene-1,4-diamine.

8. The compound according to claim 1, wherein the compound is in the form of a salt.

9. The compound according to claim 8, wherein the compound is in the form of an acid addition salt chosen from the hydrochlorides, hydrobromides, sulfates, citrates, succinates, tartrates, lactates, tosylates, benzenesulfonates, phosphates and acetates.

10. A process for preparing a compound of formula (I):

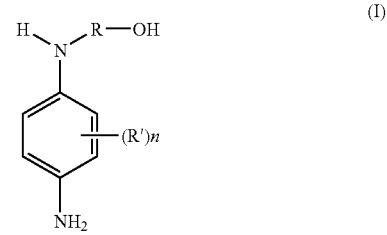

wherein:
R is chosen from linear and branched C₃-C₁₀ alkylene radicals, which are optionally substituted with at least one group chosen from amino, monoalkylamino, dialkylamino, alkylcarbonyl, amido, monoalkylaminocarbonyl and dialkylaminocarbonyl groups, wherein the alkylene radicals are interrupted with at least one heteroatom chosen from nitrogen and oxygen,
R' is chosen from alkyl, alkoxy, hydroxyalkoxy, alkoxyalkyl, monohydroxyalkyl and polyhydroxyalkyl radicals and a chlorine atom, and
n is an integer from 1 to 4;
comprising the reduction of nitro compounds of formula (II):

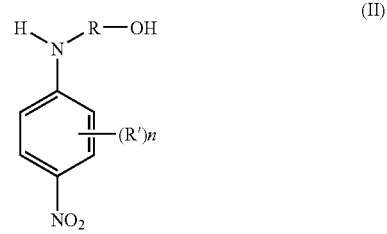

wherein:
R is chosen from linear and branched C₃-C₁₀ alkylene radicals, optionally substituted with at least one group chosen from amino, monoalkylamino, dialkylamino, alkylcarbonyl, amido, monoalkylaminocarbonyl, and dialkylaminocarbonyl groups, wherein the alkylene radicals are interrupted with at least one heteroatom chosen from nitrogen and oxygen, R' is chosen from alkyl, alkoxy, hydroxyalkoxy, alkoxyalkyl, monohydroxyalkyl and polyhydroxyalkyl radicals, and a chlorine atom, and n is an integer from 1 to 4.

11. A cosmetic composition for dyeing fibers, comprising, in a medium that is suitable for dyeing, at least one dye compound of formula (I):

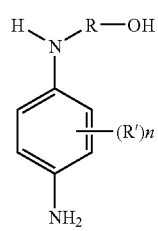

wherein:
R is chosen from linear and branched $C_3$-$C_{10}$ alkylene radicals, which are optionally substituted with at least one group chosen from amino, monoalkylamino, dialkylamino, alkylcarbonyl, amido, monoalkylaminocarbonyl and dialkylaminocarbonyl groups, wherein the alkylene radicals are interrupted with at least one heteroatom chosen from nitrogen and oxygen, R' is chosen from alkyl, alkoxy, hydroxyalkoxy, alkoxyalkyl, monohydroxyalkyl and polyhydroxyalkyl radicals and a chlorine atom, and n is an integer from 1 to 4.

12. The cosmetic composition according to claim 11, wherein the at least one dye compound of formula (I) is present in an amount ranging from 0.0001% to 20% by weight, relative to the total weight of the composition.

13. The cosmetic composition according to claim 12, wherein the at least one dye compound of formula (I) is present in an amount ranging from 0.005% to 6% by weight, relative to the total weight of the composition.

14. The cosmetic composition according to claim 11, wherein the medium that is suitable for dyeing consists of water, or comprises a mixture of water and at least one organic solvent chosen from branched and unbranched $C_1$-$C_4$ lower alcohols; polyols and polyol ethers, propylene glycol, propylene glycol monomethyl ether, diethylene glycol monoethyl ether, monomethyl ether, glycerol, and aromatic alcohols.

15. The cosmetic composition according to claim 11, further comprising at least one cosmetic adjuvant chosen from antioxidants, penetrating agents, sequestering agents, fragrances, buffers, dispersants, surfactants, conditioning agents, film-forming agents, polymers, ceramides, preserving agents, nacreous agents, opacifiers, vitamins and provitamins.

16. The cosmetic composition according to claim 15, wherein the at least one cosmetic adjuvant is, for each cosmetic adjuvant present, present in an amount ranging from 0.01% to 20% by weight, relative to the weight of the composition.

17. The cosmetic composition according to claim 11, further comprising at least one additional oxidation dye precursor other than the dye compounds of formula (I).

18. The cosmetic composition according to claim 17, wherein the at least one additional oxidation dye precursor is an oxidation coupler chosen from meta-phenylenediamines, meta-aminophenols, meta-diphenols, naphthalene-based couplers, heterocyclic couplers, and the addition salts thereof.

19. The cosmetic composition according to claim 18, wherein the at least one coupler is present in an amount ranging from 0.0001% to 20% by weight, relative to the total weight of the composition.

20. The cosmetic composition according to claim 17, wherein the at least one additional oxidation dye precursor other than the dye compounds of formula (I) is an oxidation base chosen from para-phenylenediamines, bis(phenyl)alkylenediamines, para-aminophenols, ortho-aminophenols, heterocyclic bases, and the addition salts thereof.

21. The cosmetic composition according to claim 20, wherein the at least one oxidation base other than the dye compounds of formula (I) is present in an amount ranging from 0.0001% to 20% by weight, relative to the total weight of the composition.

22. The cosmetic composition according to claim 11, further comprising at least one direct dye chosen from natural and cationic direct dyes.

23. A ready-to-use dye composition, comprising the mixture of
a composition comprising, in a medium that is suitable for dyeing, at least one dye compound of formula (I):

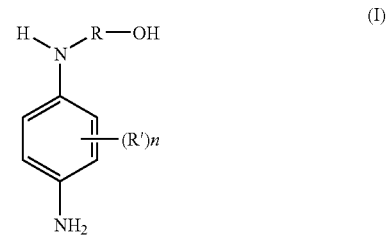

wherein:
R is chosen from linear and branched $C_3$-$C_{10}$ alkylene radicals, which are optionally substituted with at least one group chosen from amino, monoalkylamino, dialkylamino, alkylcarbonyl, amido, monoalkylaminocarbonyl and dialkylaminocarbonyl groups, wherein the alkylene radicals are interrupted with at least one heteroatom chosen from nitrogen and oxygen, R' is chosen from alkyl, alkoxy, hydroxyalkoxy, alkoxyalkyl, monohydroxyalkyl and polyhydroxyalkyl radicals and a chlorine atom, and n is an integer from 1 to 4; and at least one oxidizing agent chosen from hydrogen peroxide, urea peroxide, alkaline metal bromates, persalts, peracids and oxidase enzymes.

24. A process for dyeing keratin fibers, comprising
applying to the keratin fibers at least one composition comprising, in a medium that is suitable for dyeing, at least one dye compound of formula (I):

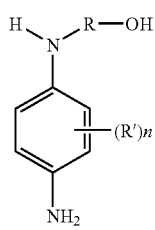

wherein:
R is chosen from linear and branched $C_3$-$C_{10}$ alkylene radicals, which are optionally substituted with at least one group chosen from amino, monoalkylamino, dialkylamino, alkylcarbonyl, amido, monoalkylaminocarbonyl and dialkylaminocarbonyl groups, wherein the alkylene radicals are interrupted with at least one heteroatom chosen from nitrogen and oxygen,
R' is chosen from alkyl, alkoxy, hydroxyalkoxy, alkoxyalkyl, monohydroxyalkyl and polyhydroxyalkyl radicals and a chlorine atom, and
n is an integer from 1 to 4;
wherein the at least one dye composition is left on the fibers for a period of time that is sufficient to develop the desired coloration, and
wherein the at least one dye composition is in the presence of at least one oxidizing agent, the oxidizing agent being applied before, simultaneously with or after the dye composition.

25. A process for dyeing keratin fibers, wherein the ready-to-use composition according to claim 23 is applied to the fibers for a period of time that is sufficient to develop the desired coloration.

26. A multi-compartment kit for dyeing keratin fibers comprising,
at least one first compartment comprising a dye composition comprising, in a medium that is suitable for dyeing, at least one dye compound of formula (I):

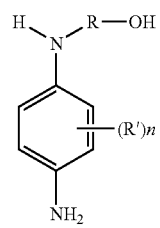

wherein:
R is chosen from linear and branched $C_3$-$C_{10}$ alkylene radicals, which are optionally substituted with at least one group chosen from amino, monoalkylamino, dialkylamino, alkylcarbonyl, amido, monoalkylaminocarbonyl and dialkylaminocarbonyl groups, wherein the alkylene radicals are interrupted with at least one heteroatom chosen from nitrogen and oxygen,
R' is chosen from alkyl, alkoxy, hydroxyalkoxy, alkoxyalkyl, monohydroxyalkyl and polyhydroxyalkyl radicals and a chlorine atom, and
n is an integer from 1 to 4; and
at least one second compartment comprising at least one oxidizing agent.

* * * * *